US011833220B2

(12) United States Patent
Jiang et al.

(10) Patent No.: US 11,833,220 B2

(45) Date of Patent: Dec. 5, 2023

(54) ARTIFICIAL MULTI-ANTIGEN FUSION PROTEIN AND PREPARATION AND USE THEREOF

(71) Applicants: OXFORD VACMEDIX UK LTD., Oxfordshire (GB); Shisong Jiang, Jiangsu (CN)

(72) Inventors: Shisong Jiang, Jiangsu (CN); Xiaobing Xia, Oxfordshire (GB); Hanghai Ding, Oxfordshire (GB)

(73) Assignees: Oxford Vacmedix UK Ltd., Oxfordshire (GB); Shisong Jiang, Jiangsu (CN)

( * ) Notice: Subject to any disclaimer, the term of this patent is extended or adjusted under 35 U.S.C. 154(b) by 41 days.

(21) Appl. No.: 15/536,428

(22) PCT Filed: Dec. 15, 2015

(86) PCT No.: PCT/CN2015/097470

§ 371 (c)(1),
(2) Date: Jun. 15, 2017

(87) PCT Pub. No.: WO2016/095812

PCT Pub. Date: Jun. 23, 2016

(65) Prior Publication Data

US 2017/0340751 A1 Nov. 30, 2017

(30) Foreign Application Priority Data

Dec. 15, 2014 (CN) ......................... 201410777861.0

(51) Int. Cl.

| | |
|---|---|
| ***A61K 39/02*** | (2006.01) |
| ***A61K 39/12*** | (2006.01) |
| ***C07K 19/00*** | (2006.01) |
| ***C12N 5/0783*** | (2010.01) |
| ***A61K 47/68*** | (2017.01) |
| ***A61K 39/118*** | (2006.01) |
| ***C12N 15/70*** | (2006.01) |
| ***C12Q 1/686*** | (2018.01) |
| *A61K 39/39* | (2006.01) |
| *C07K 2/00* | (2006.01) |
| *C07K 16/00* | (2006.01) |

(52) U.S. Cl.

CPC .......... *A61K 47/6849* (2017.08); *A61K 39/02* (2013.01); *A61K 39/118* (2013.01); *A61K 39/12* (2013.01); *A61K 47/6855* (2017.08); *C07K 19/00* (2013.01); *C12N 5/0636* (2013.01); *C12N 15/70* (2013.01); *C12Q 1/686* (2013.01); *A61K 39/39* (2013.01); *C07K 2/00* (2013.01); *C07K 16/00* (2013.01); *C12N 2501/505* (2013.01)

(58) Field of Classification Search

None

See application file for complete search history.

(56) References Cited

U.S. PATENT DOCUMENTS 5,693,325 A * 12/1997 Kahn .................. C07K 14/005 424/188.1
7,179,645 B2 * 2/2007 Humphreys ........... C07H 21/04 435/320.1

FOREIGN PATENT DOCUMENTS

| | | |
|---|---|---|
| CN | 101745104 | 6/2010 |
| CN | 102343103 | 2/2012 |
| CN | 103180343 | 6/2013 |
| WO | 2007125371 A2 | 11/2007 |
| WO | WO2007125371 A2 * | 11/2007 |
| WO | 2011/146559 | 11/2011 |

OTHER PUBLICATIONS

Celis et al (Mol. Immunol. 1994, 31(8): 1423-1430) (Year: 1994).*
Ochoa-Garay et al (Molec. Immunol. 1997, 34(3): 273-281) (Year: 1997).*
Karin et al (JEM, 1994, 180: 2227-2237) (Year: 1994).*
HLA Nomenclature 2015 (Year: 2015).*
Haen and Rammensee (Curr. Opin. Immunol. 2013, 25: 277-283) (Year: 2013).*
Riley, E.M. (Symposia of the Brit. Soc. For Parasitol., 1996, 33: abstract of pp. 539-551) (Year: 1996).*
Current Protocols in Protein Science, 2002: 22.1.- 22.1.19) (Year: 2002).*
Bazhan et al.(Mol. Immunol. 2010, 47: 1507-1515) (Year: 2010).*
Newman et al (Front. Biosci., 2002, 7 d1503-1515) (Year: 2002).*
Zhao et al (Antiviral Res. 2012, 93: 260-269) (Year: 2012).*
Antonets et al (CAPLUS abstract of Patent RU 2522830, date Jul. 20, 2014) (Year: 2014).*
Lu, S (Curr. Opin. Immunol. 2009, 21: 346-351) (Year: 2009).*
Bremel and Homan (Immunome Res., Nov. 2, 2010, 6(8): 1-21) (Year: 2010).*
Pluger et al (Eur. J. Immunol. 2002, 32: 467-476) (Year: 2002).*
Choe et al (J. Biol. Chem. 2006, 281: 12824-12832) (Year: 2006).*
Schumacher and Schrieber (Science, 2015, 384 (6230): 69-74) (Year: 2015).*
Eisenlohr et al (J. Exp. Med. 1992, 175: 481-487) (Year: 1992).*
Shastri et al (J. Immunol. 1995, 155: 4339-4346) (Year: 1995).*

(Continued)

*Primary Examiner* — G. R. Ewoldt

*Assistant Examiner* — Marianne DiBrino

(74) *Attorney, Agent, or Firm* — HAMRE, SCHUMANN, MUELLER & LARSON, P.C.

(57) ABSTRACT

Provided are an artificial multi-antigen fusion protein and a preparation method thereof. The fusion protein can effectively stimulate CD8+T and CD4+ T cell immunities, and can be applied to immunodiagnostics or serve as a prophylactic or therapeutic vaccine.

10 Claims, 5 Drawing Sheets

Specification includes a Sequence Listing.

(56) References Cited

OTHER PUBLICATIONS

Bergmann et al (J. Immunol. 1996, 157: 3242-3249) (Year: 1996).*
Wang et al (Cell. Immunol. 1992, 143: 284-297) (Year: 1992).*
Perkins et al (J. Immunol. 1991, 146(7): 2137-2144) (Year: 1991).*
Theobald et al (J. Exp. Med. 1998, 188(6): 1017-1028) (Year: 1998).*
Gileadi et al (Eur. J. Immunol. 1999, 29: 2213-2222) (Year: 1999).*
Ruckrich et al (Biol. Chem. 2006, 387: 1503-1511) (Year: 2006).*
International Search Report for international application No. PCT/CN2015/097470, dated Mar. 23, 2016 (8 pages, Including English translation).
The extended European Search Report issued in European Patent Application No. 15869319.2, dated May 23, 2018, 9 pages provided.
The Examination Report issued in European Patent Application No. 15869319.2, dated Dec. 12, 2019, 4 pages provided.
Office Action issued in Japanese Patent Application No. 2017-533496, dated Nov. 19, 2019, with English translation, 10 pages provided.
Shen et al., "Important Role of Cathepsin S in Generating Peptides for TAP-Independent MHC Class I Crosspresentation In Vivo", Immunity, vol. 21, Issue 2, Aug. 2004, pp. 155-165, 11 pages provided, cited in corresponding Japanese Office Action.
Zhang et al., "Comparing pooled peptides with intact protein for accessing cross-presentation pathways for protective CD8+ and CD4+ T cells.", The Journal of Biological Chemistry, vol. 284, Issue 14, Apr. 3, 2009, pp. 9184-9191, cited in corresponding Japanese Office Action.
Rosalia et al., "Dendritic cells process synthetic long peptides better than whole protein, improving antigen presentation and T-cell activation", Eur J Immunol, Oct. 2013, 43(10), pp. 2554-2565, Cited in EESR issued May 23, 2018.
Cai et al., "Protective cellular immunity generated by cross-presenting recombinant overlapping peptide proteins", Oncotarget, Advance Publications, Aug. 24, 2017, 8 (44), 9 pages provided, Cited in EESR issued May 23, 2018.
Welters et al., "Induction of Tumor-Specific CD4+ and CD8+ T-Cell Immunity in Cervical Cancer Patients by a Human Papillomavirus Type 16 E6 and E7 Long Peptides Vaccine", Clinical Cancer Research, Published Jan. 1, 2008, 14 (1), pp. 178-187, Cited in EESR issued May 23, 2018.
Sabbatini et al., "Phase I Trial of Overlapping Long Peptides from a Tumor Self-Antigen and Poly-ICLC Shows Rapid Induction of Integrated Immune Response in Ovarian Cancer Patients", Clinical Cancer Research, Published OnlineFirst Oct. 2, 2012, 13 pages provided, 18 (23) : 6497-6508.
van Poelgeest et al., "HPV16 synthetic long peptide (HPV16-SLP) vaccination therapy of patients with advanced or recurrent HPV16-induced gynecological carcinoma, a phase II trial", Journal of Translational Medicine, 2013, 14 pages provided, 11: 1-14.
Rosalia et al., "Dendritic cells process synthetic long peptides better than whole protein, improving antigen presentation and T-cell activation", European Journal of Immunology, 2013, 12 pages provided, 43: 2554-2565.
Kenter et al., "Vaccination against HPV-16 Oncoproteins for Vulvar Intraepithelial Neoplasia", The New England Journal of Medicine, Nov. 5, 2009, 10 pages provided, vol. 361, 1838-1847.
Melief et al., "Immunotherapy of established (pre)malignant disease by synthetic long peptide vaccines", Nature Reviews, vol. 8, May 2008, 10 pages provided, pp. 351-360.

* cited by examiner

SEQUENCE LISTING

<160> NUMBER OF SEQ ID NOS: 26

<210> SEQ ID NO 1
<211> LENGTH: 282
<212> TYPE: PRT
<213> ORGANISM: Artificial Sequence
<220> FEATURE:
<223> OTHER INFORMATION: ESAT6-CFP10 antigen fusion protein
<220> FEATURE:
<221> NAME/KEY: misc_feature
<223> OTHER INFORMATION: ESAT6-CFP10 antigen fusion protein

<400> SEQUENCE: 1

Met Ala Glu Met Lys Thr Asp Ala Ala Thr Leu Ala Gln Glu Ala Gly
1 5 10 15

Asn Phe Glu Arg Ile Ser Gly Asp Leu Lys Thr Gln Ile Asp Gln Val
20 25 30

Glu Ser Thr Leu Arg Met Lys Thr Gln Ile Asp Gln Val Glu Ser Thr
35 40 45

Ala Gly Ser Leu Gln Gly Gln Trp Arg Gly Ala Ala Gly Thr Ala Ala
50 55 60

Gln Ala Ala Val Val Arg Phe Gln Glu Leu Arg Met Lys Ala Gln Ala
65 70 75 80

Ala Val Val Arg Phe Gln Glu Ala Ala Asn Lys Gln Lys Gln Glu Leu
85 90 95

Asp Glu Ile Ser Thr Asn Ile Arg Gln Ala Gly Val Gln Tyr Ser Arg
100 105 110

Leu Arg Met Lys Ile Arg Gln Ala Gly Val Gln Tyr Ser Arg Ala Asp
115 120 125

Glu Glu Gln Gln Gln Ala Leu Ser Ser Gln Met Gly Phe Leu Arg Met
130 135 140

Lys Met Thr Glu Gln Gln Trp Asn Phe Ala Gly Ile Glu Ala Ala Ala
145 150 155 160

Ser Ala Ile Gln Gly Asn Val Thr Ser Ile His Ser Leu Leu Asp Glu
165 170 175

Gly Lys Gln Ser Leu Arg Met Lys His Ser Leu Leu Asp Glu Gly Lys

-continued

```
            180                 185                 190

Gln Ser Leu Thr Lys Leu Ala Ala Ala Trp Gly Gly Ser Gly Ser Glu
        195                 200                 205

Ala Tyr Gln Gly Val Gln Gln Lys Trp Asp Ala Leu Arg Met Lys Tyr
    210                 215                 220

Gln Gly Val Gln Gln Lys Trp Asp Ala Thr Ala Thr Glu Leu Asn Asn
225                 230                 235                 240

Ala Leu Gln Asn Leu Ala Arg Thr Ile Ser Glu Ala Gly Gln Ala Met
                245                 250                 255

Ala Ser Leu Arg Met Lys Ile Ser Glu Ala Gly Gln Ala Met Ala Ser
            260                 265                 270

Thr Glu Gly Asn Val Thr Gly Met Phe Ala
        275                 280


<210> SEQ ID NO 2
<211> LENGTH: 849
<212> TYPE: DNA
<213> ORGANISM: Artificial Sequence
<220> FEATURE:
<223> OTHER INFORMATION: Encoding sequence of ESAT6-CFP10 antigen fusion
      protein
<220> FEATURE:
<221> NAME/KEY: misc_feature
<223> OTHER INFORMATION: encoding sequence of ESAT6-CFP10 antigen fusion
      protein

<400> SEQUENCE: 2

atggccgaaa tgaaaaccga tgcagcaacc ctggcacaag aagcaggtaa ttttgaacgt     60

attagcggtg atctgaaaac ccagattgat caggttgaaa gcaccctgcg tatgaaaaca    120

caaatcgatc aagtggaaag taccgcaggt agcctgcagg gtcagtggcg tggtgcagca    180

ggcaccgcag cacaggcagc agttgttcgt tttcaagaac tgcgcatgaa agcccaggca    240

gccgtggtgc gcttccaaga agccgcaaat aaacagaaac aagagctgga tgaaatcagc    300

accaatattc gtcaggcagg cgttcagtat agccgtttac ggatgaaaat tcgtcaagcc    360

ggtgtgcagt attcacgtgc agatgaagaa cagcagcaag cactgagcag ccagatgggt    420

tttttaagaa tgaaaatgac cgagcagcag tggaattttg caggtattga agcagccgca    480

agcgcaattc agggtaatgt taccagcatt catagcctgc tggacgaagg taaacagagc    540

ctgcggatga agcatagtct gttagatgaa ggcaaacagt cactgaccaa actggcagca    600

gcatggggtg gtagcggtag cgaagcatat cagggtgttc agcagaaatg ggatgcatta    660

cgtatgaagt atcagggcgt gcaacaaaag tgggacgcaa ccgcaaccga actgaataat    720

gcactgcaga atctggcacg taccattagt gaagccggtc aggcaatggc cagcttacgc    780

atgaagattt ctgaagcagg ccaagctatg gcaagcaccg aaggcaatgt gaccggtatg    840

tttgcataa                                                            849


<210> SEQ ID NO 3
<211> LENGTH: 152
<212> TYPE: PRT
<213> ORGANISM: Artificial Sequence
<220> FEATURE:
<223> OTHER INFORMATION: OVA antigen fusion protein
<220> FEATURE:
<221> NAME/KEY: misc_feature
<223> OTHER INFORMATION: OVA antigen fusion protein

<400> SEQUENCE: 3

Met Leu Val Leu Leu Pro Asp Glu Val Ser Gly Leu Glu Gln Leu Glu
```

-continued

```
1               5                   10                  15

Ser Ile Ile Asn Phe Glu Lys Leu Thr Glu Trp Thr Ser Ser Leu Arg
            20                  25                  30

Met Lys Leu Glu Ser Ile Ile Asn Phe Glu Lys Leu Thr Glu Trp Thr
        35                  40                  45

Ser Ser Asn Val Met Glu Glu Arg Lys Ile Lys Val Tyr Leu Pro Arg
    50                  55                  60

Met Lys Met Glu Glu Lys Tyr Asn Leu Thr Ser Val Leu Met Ala Met
65                  70                  75                  80

Gly Ile Thr Asp Val Phe Ser Ser Ser Ala Asn Leu Ser Gly Ile Ser
                85                  90                  95

Ser Ala Glu Ser Leu Lys Ile Ser Gln Ala Val His Ala Ala His Ala
            100                 105                 110

Glu Ile Asn Glu Ala Gly Arg Leu Arg Met Lys Ile Ser Gln Ala Val
        115                 120                 125

His Ala Ala His Ala Glu Ile Asn Glu Ala Gly Arg Glu Val Val Gly
    130                 135                 140

Ser Ala Glu Ala Gly Val Asp Ala
145                 150


<210> SEQ ID NO 4
<211> LENGTH: 459
<212> TYPE: DNA
<213> ORGANISM: Artificial Sequence
<220> FEATURE:
<223> OTHER INFORMATION: encoding sequence of OVA antigen fusion protein
<220> FEATURE:
<221> NAME/KEY: misc_feature
<223> OTHER INFORMATION: encoding sequence of OVA antigen fusion protein

<400> SEQUENCE: 4

atgctggttc tgctgccgga tgaagttagc ggtctggaac agctggaaag cattatcaat     60

tttgaaaaac tgaccgaatg gaccagcagc ctgcgtatga aactggaatc catcattaac    120

ttcgagaaac tgacagagtg gacaagcagc aatgttatgg aagaacgtaa aatcaaagtg    180

tacctgcctc gcatgaaaat ggaagagaaa tataacctga ccagcgttct gatggcaatg    240

ggtattaccg atgtttttag cagcagcgca aatctgagcg gtattagcag cgcagaaagc    300

ctgaaaatta gccaggcagt tcatgcagca catgccgaaa ttaatgaagc aggtcgtctg    360

cggatgaaaa tttcacaggc cgtgcatgct gcccatgcag aaatcaacga agctggccgt    420

gaagttgttg gtagtgccga agccggtgtt gatgcataa                           459


<210> SEQ ID NO 5
<211> LENGTH: 140
<212> TYPE: PRT
<213> ORGANISM: Artificial Sequence
<220> FEATURE:
<223> OTHER INFORMATION: HPV16-E7 antigen fusion protein
<220> FEATURE:
<221> NAME/KEY: misc_feature
<223> OTHER INFORMATION: HPV16-E7 antigen fusion protein

<400> SEQUENCE: 5

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Leu Arg Met Lys Glu Gln Leu Asn Asp Ser Ser Glu Glu
        35                  40                  45
```

-continued

```
Glu Asp Glu Ile Asp Gly Pro Ala Gly Gln Ala Glu Pro Asp Arg Ala
    50                  55                  60

His Tyr Asn Ile Val Thr Phe Cys Cys Lys Leu Arg Met Lys His Tyr
65                  70                  75                  80

Asn Ile Val Thr Phe Cys Cys Lys Cys Asp Ser Thr Leu Arg Leu Cys
                85                  90                  95

Val Gln Ser Thr His Val Asp Ile Arg Thr Leu Glu Asp Leu Leu Met
            100                 105                 110

Gly Leu Arg Met Lys Ile Arg Thr Leu Glu Asp Leu Leu Met Gly Thr
        115                 120                 125

Leu Gly Ile Val Cys Pro Ile Cys Ser Gln Lys Pro
    130                 135                 140
```

<210> SEQ ID NO 6
<211> LENGTH: 423
<212> TYPE: DNA
<213> ORGANISM: Artificial Sequence
<220> FEATURE:
<223> OTHER INFORMATION: encoding sequence of HPV16-E7 antigen fusion protein
<220> FEATURE:
<221> NAME/KEY: misc_feature
<223> OTHER INFORMATION: encoding sequence of HPV16-E7 antigen fusion protein

<400> SEQUENCE: 6

```
atgcatggtg ataccccgac cctgcatgaa tatatgctgg atctgcaacc ggaaaccacc     60

gatctgtatt gttatgagca gctgaatgat agcagcgaag aggaattacg catgaaggaa    120

cagctgaacg attcaagcga agaagaggac gaaattgacg gtccggcagg tcaggcagaa    180

ccggatcgtg cacattacaa cattgttacc ttttgttgca aactgagaat gaaacactac    240

aatatcgtga ccttctgctg taaatgtgat agcaccctgc gtctgtgtgt tcagagcacc    300

catgttgata ttcgtacatt agaggacctg ctgatgggcc tgcggatgaa aattcgtacc    360

ctggaagacc tgttaatggg caccctgggt attgtttgtc cgatttgtag ccagaaaccg    420

taa                                                                  423
```

<210> SEQ ID NO 7
<211> LENGTH: 15
<212> TYPE: DNA
<213> ORGANISM: Artificial Sequence
<220> FEATURE:
<223> OTHER INFORMATION: Polynucleotide
<220> FEATURE:
<221> NAME/KEY: misc_feature
<223> OTHER INFORMATION: Polynucleotide

<400> SEQUENCE: 7

```
tacttccaat ccatg                                                      15
```

<210> SEQ ID NO 8
<211> LENGTH: 18
<212> TYPE: DNA
<213> ORGANISM: Artificial Sequence
<220> FEATURE:
<223> OTHER INFORMATION: Polynucleotide
<220> FEATURE:
<221> NAME/KEY: misc_feature
<223> OTHER INFORMATION: Polynucleotide

<400> SEQUENCE: 8

```
tatccacctt tactgtta                                                   18
```

<210> SEQ ID NO 9
<211> LENGTH: 4
<212> TYPE: PRT
<213> ORGANISM: Artificial Sequence
<220> FEATURE:
<223> OTHER INFORMATION: cleavage site of cathepsin S

<400> SEQUENCE: 9

Leu Arg Met Lys
1

<210> SEQ ID NO 10
<211> LENGTH: 4
<212> TYPE: PRT
<213> ORGANISM: Artificial Sequence
<220> FEATURE:
<223> OTHER INFORMATION: cleavage site of cathepsin B

<400> SEQUENCE: 10

Met Lys Arg Leu
1

<210> SEQ ID NO 11
<211> LENGTH: 4
<212> TYPE: PRT
<213> ORGANISM: Artificial Sequence
<220> FEATURE:
<223> OTHER INFORMATION: cleavage site of cathepsin K

<400> SEQUENCE: 11

His Pro Gly Gly
1

<210> SEQ ID NO 12
<211> LENGTH: 4
<212> TYPE: PRT
<213> ORGANISM: Artificial Sequence
<220> FEATURE:
<223> OTHER INFORMATION: cleavage site of cathepsin S

<400> SEQUENCE: 12

Arg Cys Gly Leu
1

<210> SEQ ID NO 13
<211> LENGTH: 4
<212> TYPE: PRT
<213> ORGANISM: Artificial Sequence
<220> FEATURE:
<223> OTHER INFORMATION: cleavage site of cathepsin S

<400> SEQUENCE: 13

Thr Val Gly Leu
1

<210> SEQ ID NO 14
<211> LENGTH: 4
<212> TYPE: PRT
<213> ORGANISM: Artificial Sequence
<220> FEATURE:
<223> OTHER INFORMATION: cleavage site of cathepsin S

<400> SEQUENCE: 14

Thr Val Gln Leu
1

<210> SEQ ID NO 15
<211> LENGTH: 4
<212> TYPE: PRT
<213> ORGANISM: Artificial Sequence
<220> FEATURE:
<223> OTHER INFORMATION: cleavage site of cathepsin S
<220> FEATURE:
<221> NAME/KEY: misc_feature
<222> LOCATION: (1)..(1)
<223> OTHER INFORMATION: Xaa can be any naturally occurring amino acid

<400> SEQUENCE: 15

Xaa Asn Leu Arg
1

<210> SEQ ID NO 16
<211> LENGTH: 4
<212> TYPE: PRT
<213> ORGANISM: Artificial Sequence
<220> FEATURE:
<223> OTHER INFORMATION: cleavage site of cathepsin S
<220> FEATURE:
<221> NAME/KEY: misc_feature
<222> LOCATION: (1)..(1)
<223> OTHER INFORMATION: Xaa can be any naturally occurring amino acid

<400> SEQUENCE: 16

Xaa Pro Leu Arg
1

<210> SEQ ID NO 17
<211> LENGTH: 4
<212> TYPE: PRT
<213> ORGANISM: Artificial Sequence
<220> FEATURE:
<223> OTHER INFORMATION: cleavage site of cathepsin S
<220> FEATURE:
<221> NAME/KEY: misc_feature
<222> LOCATION: (1)..(1)
<223> OTHER INFORMATION: Xaa can be any naturally occurring amino acid

<400> SEQUENCE: 17

Xaa Ile Val Gln
1

<210> SEQ ID NO 18
<211> LENGTH: 4
<212> TYPE: PRT
<213> ORGANISM: Artificial Sequence
<220> FEATURE:
<223> OTHER INFORMATION: cleavage site of cathepsin S
<220> FEATURE:
<221> NAME/KEY: misc_feature
<222> LOCATION: (1)..(1)
<223> OTHER INFORMATION: Xaa can be any naturally occurring amino acid

<400> SEQUENCE: 18

Xaa Arg Met Lys
1

<210> SEQ ID NO 19
<211> LENGTH: 6
<212> TYPE: PRT
<213> ORGANISM: Artificial Sequence
<220> FEATURE:
<223> OTHER INFORMATION: label sequence

<400> SEQUENCE: 19

His His His His His His 1 5

<210> SEQ ID NO 20
<211> LENGTH: 7
<212> TYPE: PRT
<213> ORGANISM: Artificial Sequence
<220> FEATURE:
<223> OTHER INFORMATION: MHC-1 epitope

<400> SEQUENCE: 20

Ser Ile Ile Asn Phe Lys Leu
1 5

<210> SEQ ID NO 21
<211> LENGTH: 8
<212> TYPE: PRT
<213> ORGANISM: Artificial Sequence
<220> FEATURE:
<223> OTHER INFORMATION: polypeptide

<400> SEQUENCE: 21

Ser Ile Ile Asn Phe Glu Lys Leu
1 5

<210> SEQ ID NO 22
<211> LENGTH: 8
<212> TYPE: PRT
<213> ORGANISM: Artificial Sequence
<220> FEATURE:
<223> OTHER INFORMATION: polypeptide

<400> SEQUENCE: 22

Ser Ile Ile Asn Phe Ile Lys Leu
1 5

<210> SEQ ID NO 23
<211> LENGTH: 370
<212> TYPE: DNA
<213> ORGANISM: Artificial Sequence
<220> FEATURE:
<223> OTHER INFORMATION: pNIC28a-Bsa4 expression vector
<220> FEATURE:
<221> NAME/KEY: misc_feature
<223> OTHER INFORMATION: pNIC28a-Bsa4 expression vector

<400> SEQUENCE: 23
ctcgatcccg cgaaattaat acgactcact ataggggaat tgtgagcgga taacaattcc 60
cctctagaaa taattttgtt taactttaag aaggagatat acatatgcac catcatcatc 120
atcattcttc tggtgtagat ctgggtaccg agaacctgta cttccaatcc atggagaccg 180
acgtccacat gatatcctat tggcattgac ggtctccagt aaaggtggat acggatccga 240
attcgagctc cgtcgacaag cttgcggccg cactcgagca ccaccaccac caccactgag 300
atccggctgc taacaaagcc cgaaaggaag ctgagttggc tgctgccacc gctgagcaat 360
aactagcata 370

<210> SEQ ID NO 24
<211> LENGTH: 190
<212> TYPE: DNA
<213> ORGANISM: Artificial Sequence
<220> FEATURE:
<223> OTHER INFORMATION: Part of pNIC28a-Bsa4 expression vector
<220> FEATURE:
<221> NAME/KEY: misc_feature
<222> LOCATION: (190)..(190)
<223> OTHER INFORMATION: last nucleotide t is attached to SacB fragment -continued

```
<400> SEQUENCE: 24

ctcgatcccg cgaaattaat acgactcact ataggggaat tgtgagcgga taacaattcc     60

cctctagaaa taattttgtt taactttaag aaggagatat acatatgcac catcatcatc    120

atcattcttc tggtgtagat ctgggtaccg agaacctgta cttccaatcc atggagaccg    180

acgtccacat                                                           190


<210> SEQ ID NO 25
<211> LENGTH: 180
<212> TYPE: DNA
<213> ORGANISM: Artificial Sequence
<220> FEATURE:
<223> OTHER INFORMATION: Part of pNIC28a-Bsa4 expression vector
<220> FEATURE:
<221> NAME/KEY: misc_feature
<222> LOCATION: (1)..(1)
<223> OTHER INFORMATION: first nucleotide G is attached to the SacB
      fragment

<400> SEQUENCE: 25

gatatcctat tggcattgac ggtctccagt aaaggtggat acggatccga attcgagctc     60

cgtcgacaag cttgcggccg cactcgagca ccaccaccac caccactgag atccggctgc    120

taacaaagcc cgaaaggaag ctgagttggc tgctgccacc gctgagcaat aactagcata    180


<210> SEQ ID NO 26
<211> LENGTH: 22
<212> TYPE: PRT
<213> ORGANISM: Artificial Sequence
<220> FEATURE:
<223> OTHER INFORMATION: N-terminal protein His-tag having Tobbaco Etch
      Virus (TEV) Protease Substrate Sequence used in pNIC28a-Bsa4
      vector

<400> SEQUENCE: 26

Met His His His His His His Ser Ser Gly Val Asp Leu Gly Thr Glu
1               5                   10                  15

Asn Leu Tyr Phe Gln Ser
            20
```

ARTIFICIAL MULTI-ANTIGEN FUSION PROTEIN AND PREPARATION AND USE THEREOF

STATEMENT REGARDING SEQUENCE LISTING

This application contains a Sequence Listing which has been submitted electronically in ASCII format and is hereby incorporated by reference in its entirety. Said ASCII copy, created on Jun. 12, 2023, is named “sequence listing.txt” and is 14,360 bytes in size.

TECHNICAL FIELD

The present invention relates to the field of medicine and, more particularly, to an artificial multi-antigen fusion protein capable of simultaneously stimulating $CD4^+$ and $CD8^+$ T cell immune responses and methods as well as uses thereof. After expressed and purified, the artificial multi-antigen fusion protein of the present invention can be directly used for immuno-diagnosis or as a prophylactic or therapeutic vaccine.

BACKGROUND

A series of changes in humor immunity and cellular immune will occur in human body due to infection with bacteria, viruses or stimulation by cancer cells. Cellular immunity is important for tumor cells and infectious bacteria and viruses that have infected and entered into cells. After the human body encounters for the first time the above exogenous stimulus, T lymphocytes will be sensitized, and converted into memory T lymphocytes. When the human body comes into contact with the same antigen again, a quickly specific immune response will be produced, including the effect of T lymphocyte response, thereby producing a variety of cytokines to exert immune effects (cellular immunity). Because cellular immunity plays an important role in the control and removal of bacteria, viruses and tumors, cellular immune vaccines play a role in the prevention of infection by bacterial and viral and cancer therapy.

Currently, there is no clinically effective drug for some intracellular infectious bacteria and viruses. Therefore, therapeutic vaccines that stimulate cell immunity play a very important role in controlling tumor and infection by bacterial and virus. At present, US FDA has approved the therapeutic vaccine for the treatment of prostate cancer.

In addition, monitoring of cellular immunity is critical to the treatment, prognosis of diseases and effectiveness of vaccines.

A commonly used method for detecting cellular immunity is enzyme linked immunospot assay (ELISPOT), which can detect T cells secreting cytokines on single cell level. For example, cellular immune function can be assessed by detecting the number of T cells secreting cytokines after stimulation by tuberculosis (TB) specific antigen. For tuberculosis, the detection of cellular immunity is one way to diagnose TB infection. In 2008, US FDA has approved a ELISPOT Commercialization Kit T-SPOT for the diagnosis of tuberculosis infection. In these diagnostic kits, a mixture of polypeptides of 18-20 amino acids is basically used as a stimulating source. These polypeptides are phagocytosed by the antigen presenting cells in peripheral blood, processed and present together with their own HLA antigens to the cell surface, and then recognized by T cell receptors of memory T lymphocytes. After being stimulated, T cells produce cytokines for example gamma interferon and therefore, can be detected.

There are many different clones of T cells in human body, wherein each clone needs to be stimulated by different short peptide with HLA; there are different T cell clones in different human bodies; and there are different HLA antigens in different human bodies. To select T cells from some HLA population, it is necessary to identify, select T cell epitope antigens from the population. Identification of HLA phenotypes and T cell epitope sequences are time-consuming and laborious work. To cover all T cell recognition epitopes of all populations and certain stimulating sources (proteins), the most common way is to synthesize a polypeptide of 18-20 amino acids or even more in length. However, for being clinically used, it is necessary to establish a strict production process and quality testing standards for each polypeptide. For example, for ESAT6 (96 amino acids) and CFP10 (100 amino acids) to be used in TB detection, a mixture of more than 20 polypeptides is typically required to cover all epitopes of the two protein antigens, resulting in high cost and expensive kits, and therefore limiting, to a certain extent, its wide application. An alternative strategy is to select a limited number of polypeptides as a source of stimulation, however, due to HLA polymorphism among different populations and difference in antigen epitopes recognized by T cell, epitope coverage is reduced by this strategy despite the reduced cost saving.

Prophylactic and therapeutic vaccines are delivered to antigen-presenting cells, especially dendritic cells (DC), and then stimulate and elicit antigen-specific cytotoxic $CD8^+$ (CTL) and helper $CD4^+$ T lymphocytes. Helper $CD4^+$ T cells can effectively stimulate and amplify cytotoxic $CD8^+$ T cells and help B cells to produce antibodies. $CD8^+$ T cells can specifically recognize and dissolve target cells containing target antigens. Activation of specific $CD8^+$ T cells depends on the antigen that can be efficiently presented to MHC class I molecule (HLA-I antigen in humans). $CD8^+$ cytotoxic T lymphocytes are the main active ingredient in prophylactic and therapeutic cellular immune vaccines because they can directly recognize and destroy tumor cells or cells infected by viruses. Therefore, most of therapeutic vaccines are designed according to how to stimulate the body to produce $CD8^+$ T cells specifically recognizing a tumor or viral antigen.

At present, it is commonly believed that only the antigen in cytoplasm of antigen-presenting cells (APC) can be degraded into small molecule peptides by proteasome and transported into endoplasmic reticulum by TAP protein, wherein CTL epitope polypeptide binds to MHC-I (HLA-I), is presented to the surface of antigen presenting cells, and binds to specific receptor of $CD8^+$ T cells, thereby specifically activating the latter. At the same time, it is also a traditional point of view that only the protein antigen transcribed and translated in cytoplasm can enter MHC-I (HLA-I) presentation pathway. Currently, it is also the core strategy for designing therapeutic vaccines, that is, development of vaccines that can be replicated, transcribed and translated in cytoplasm. If a protein antigen is phagocytosed by a cell, the antigen will not enter cytoplasm, but into endosome and lysosomes; therefore, the protein antigen can not effectively stimulate $CD8^+$ T cells.

Currently, vaccines which can effectively stimulating $CD8^+$ T cells include DNA vaccines, epitope polypeptide vaccines and bacterial or viral vector vaccines. These vaccines have some obvious drawbacks: the efficiency of DNA vaccines to enter cells is low and there is a risk of integration into genome; a single epitope polypeptide vaccine covers a very small population, thus reducing its use; bacterial/viral vector vaccine has side effects, and immunity against the vector itself is prone to be elicited in the body, thus reducing the immunity against the target antigen. Additionally, many populations may possess immunity against these bacteria/viruses before they are immunized, and therefore the vaccine is destroyed before it takes effect, thereby significantly reducing its uses.

Protein vaccine is a safe vaccine since a protein can not be self-replicated. In general, proteins are phagocytosed into endosomes and lysosomes by antigen presentation cells (APC), so that they won't enter cytoplasm and can not be degraded by cytoplasmic proteasomes and presented to MHC-Class I molecules, and the protein antigen vaccine does not stimulate CTL response. A protein is phagocytosed into APC cells, then enters lysosome, and is degraded into small molecule peptides, and then some polypeptides (CD4 epitopes) bind to MHC-Class II molecules on lysosomal membrane and are presented to cell surface to stimulate $CD4^+$ T cells. $CD4^+$ can help B cells produce antibodies. Additionally, a protein vaccine can stimulate B cells. Therefore, protein antigens have been mainly used to stimulate body to produce antibodies. Studies have found that APC can also intake antigens from outside, and present them to MHC-class I molecules, thus stimulating CTL. This process is called antigen cross presentation. However, the efficiency of this process is very low, so that no one can design a protein vaccine which can stimulate $CD8^+$ T cell immune.

Similarly, the best way for preparing a wide range of peptide-based vaccines is to prepare a series of polypeptides due to the limitation on human HLA, so that their sequences can cover all CD4 and CD8 epitopes of a protein, however, it is necessary to establish a strict production process and quality testing standards for each polypeptide, resulting in high cost and difficulties in industrialization.

Summing up, currently there is no satisfactory vaccines that can stimulate $CD8^+$ T cell immunity. Therefore, there is an urgent need in the art for developing new vaccines that are effective in stimulating $CD8^+$ T cell immunity, easily quality-controlled and of high safety.

SUMMARY OF THE INVENTION

It is an object of the present invention to provide a protein vaccine with advantages of effectively stimulate $CD8^+$ T cell immunity, easily quality-controlled and of high safety.

In the first aspect of the present invention, an artificial multi-antigen fusion protein is provided, wherein, when administered to a mammalian subject, the artificial multi-antigen fusion protein simultaneously stimulates $CD4^+$ and $CD8^+$ T cell immune responses in said subject.

In another preferred embodiment, the $CD4^+$ T cell immune response and $CD8^+$ T cell immune response result in the recognition of target cells carrying the antigen on the cell surface by the T cells.

In another preferred embodiment, the antigen in the artificial multi-antigen fusion protein is derived from a virus, a bacterium, a parasite, a *chlamydia*, a tumor cell, or a combination thereof.

In another preferred embodiment, the artificial multi-antigen fusion protein comprises ≥3, preferably ≥5, more preferably ≥10 antigen segments.

In another preferred embodiment, the upper limit of the number of antigen segments is ≤200, preferably ≤100, more preferably ≤50.

In another preferred embodiment, each antigen segment may be different, partially identical, or completely identical.

In another preferred embodiment, each antigen segment is from the same or different pathogens, or from the same or different species, or each antigen segment is an artificial sequence (i.e., artificially designed sequence, which is not present in nature).

In another preferred embodiment, each antigen segment is from a protein or a plurality of different proteins.

In another preferred embodiment, each antigen segment is from a viral antigen, a bacterial antigen, a parasitic antigen, a chlamydial antigen, a tumor antigen, or a combination thereof.

In another preferred embodiment, each antigen segment comprises at least one (preferably at least 2) $CD8^+$ epitope or a motif sequence capable of stimulating $CD8^+$ T cell immune response; and at least one (preferably at least 2) $CD4^+$ epitope or a motif sequence capable of stimulating $CD4^+$ T cell immune response.

In another preferred embodiment, each antigen segment comprises at least one (preferably at least 2) amino acid sequence simultaneously serving as $CD8^+$ epitope and $CD4^+$ epitope.

In another preferred embodiment, each antigen segment is of 8-50 amino acids, preferably 10-40 amino acids, more preferably 15-35 amino acids in length.

In another preferred embodiment, the artificial multi-antigen fusion protein further comprises sequences of cleavage site located between antigen segments.

In another preferred embodiment, the sequence of cleavage site comprises a cleavage site of cathepsin.

In another preferred embodiment, the cleavage site of cathepsin is selected from a group consisting of a cleavage site of cathepsin S (e.g., Leu-Arg-Met-Lys (SEQ ID NO: 9) or a similar cleavage site), a cleavage site of cathepsin B (e.g., Met-Lys-Arg-Leu (SEQ ID NO: 10) or a similar cleavage site), a cleavage site of cathepsin K (e.g., His-Pro-Gly-Gly (SEQ ID NO: 11) or a similar restriction site), or combinations thereof.

In another preferred embodiment, the cleavage site of cathepsin S is selected from a group consisting of Arg-Cys-Gly↓-Leu (SEQ ID NO: 12), Thr-Val-Gly↓-Leu (SEQ ID NO: 13), Thr-Val-Gln↓-Leu (SEQ ID NO: 14), X-Asn-Leu-Arg↓(SEQ ID NO: 15), X-Pro-Leu-Arg (SEQ ID NO: 16), X-Ile-Val-Gln↓ (SEQ ID NO: 17) and X-Arg-Met-Lys↓ (SEQ ID NO: 18); wherein each X is independently any natural amino acid, and ↓ represents cleavage position.

In another preferred embodiment, the cleavage site of cathepsin S is X-Arg-Met-Lys (SEQ ID NO: 18) (e.g., Leu-Arg-Met-Lys, SEQ ID NO: 9), X-Ile-Val-Gln (SEQ ID NO: 17), or a combination thereof.

In another preferred embodiment, each antigen segment is directly connected in the artificial multi-antigen fusion protein via said sequence of cleavage site.

In another preferred embodiment, the sequence of cleavage site used to connect each antigen segment is the same or different.

In another preferred embodiment, the sequence of cleavage site used to connect each antigen segment is the same.

In another preferred embodiment, the sequence of cleavage site is not contained in each antigen segment; or the sequence of cleavage site is contained in the antigen segment, while at least one cleavage product (or some or all of the cleavage products) formed after the antigen segment is digested can still be used as $CD8^+$ epitope or $CD4^+$ epitope.

In another preferred embodiment, the artificial multi-antigen fusion protein further comprises a sequence of one or more optional elements selected from a group consisting of:

(a) a label sequence (e.g., 6His, SEQ ID NO: 19, for purification);
(b) a signal peptide sequence;
(c) a membrane-penetrating sequence (e.g., CPP)
(d) an adjuvant element sequence (e.g., LRMK, SEQ ID NO: 9);
(e) a cell necrosis inductive factor sequence.

In another preferred embodiment, the artificial multi-antigen fusion protein is of 100-2000 amino acids, preferably 150-1500 amino acids, more preferably 200-1000 amino acids or 300-800 amino acids in length.

In another preferred embodiment, the mammal includes human, domestic animal (e.g., cattle, sheep, pig), pet (e.g., dog, cat), rodent, rabbit, monkey and the like.

In another preferred embodiment, the antigen segment in the antigen fusion protein covers ≥10%, ≥20%, ≥30%, ≥40%, ≥50, ≥60%, ≥70%, ≥80%, ≥90%, more preferably 100% of the amino acid sequence of one or two, or more target proteins.

In another preferred embodiment, the fusion protein is shown in the structure of formula I:

Y-(A-C)n-Z (I)

Wherein,
A is an antigen segment;
C is a sequence of cleavage site of cathepsin;
n is a positive integer ≥3;
Y is absent or is a sequence represented by "Y0-B", wherein Y0 is a signal peptide sequence, a tag sequence, a membrane-penetrating element sequence, an adjuvant element sequence, a cell necrosis-inductive element sequence, or any combination of the above sequences, and B is absent or a sequence of cleavage site;
Z is absent, or a tag sequence, a membrane-penetrating element sequence, an adjuvant element sequence, a cell necrosis-inductive element sequence, or any combination of the above sequences;
provided that when Z is absent, C in the last "A-C" can be absent.

In another preferred embodiment, the cleavage site sequence is different from C (i.e., B≠C). In another preferred embodiment, the cleavage site sequence is identical to C (i.e., B=C).

In another preferred embodiment, n is any integer from 5 to 100, preferably from 6 to 50, more preferably from 7 to 30.

In the second aspect of the present invention, a composition is provided, comprising the artificial multi-antigen fusion protein according to the first aspect of the invention and a pharmaceutically acceptable carrier.

In another preferred embodiment, the composition includes a pharmaceutical composition and a vaccine composition.

In another preferred embodiment, the dosage form of the composition includes: an injection, a lyophilized powder, a liquid formulation, an oral formulation, or a transdermal formulation.

In the third aspect of the present invention, use of the artificial multi-antigen fusion protein according to the first aspect of the present invention is provided, which is used for the preparation of a prophylactic and/or therapeutic vaccine composition or pharmaceutical composition.

In another preferred embodiment, the vaccine composition includes an anti-pathogen (e.g., a virus) vaccine composition, and an anti-tumor vaccine composition.

In another preferred embodiment, the pharmaceutical composition is used for the treatment and/or prevention of a disease selected from the group consisting of a bacterial associated disease, a virus associated disease, an autoimmune disease, a tumor associated disease, or a combination thereof.

In the fourth aspect of the present invention, use of the artificial multi-antigen fusion protein according to the first aspect of the present invention is provided, which is used for preparing an agent or a kit for detecting specific T cell immunity.

In another preferred embodiment, the specific T cell immunity includes $CD4^+$ T cell immunity and $CD8^+$ T cell immunity.

In another preferred embodiment, such agent or kit is used in skin tests.

In the fifth aspect of the present invention, a method (e.g., a therapeutic or prophylactic method) is provided, comprising steps of: administering the artificial multi-antigen fusion protein according to the first aspect of the present invention or the composition according to the second aspect of the present invention to a subject in need thereof.

In another preferred embodiment, the method is used for the treatment and/or prevention of an infection of pathogen or a tumor.

In another preferred embodiment, the subject includes both human and non-human mammals.

In another preferred embodiment, the manner of administration includes intravenous, subcutaneous, oral, transdermal administration, and the like.

It is to be understood that, within the scope of the present invention, the above-described technical features of the present invention and the technical features specifically described in the following (e.g., examples) may be combined with each other to form a new or preferred technical solution, which is not necessary to be listed one by one due to the limited contents.

MODES FOR CARRYING OUT THE INVENTION

Figure 1:
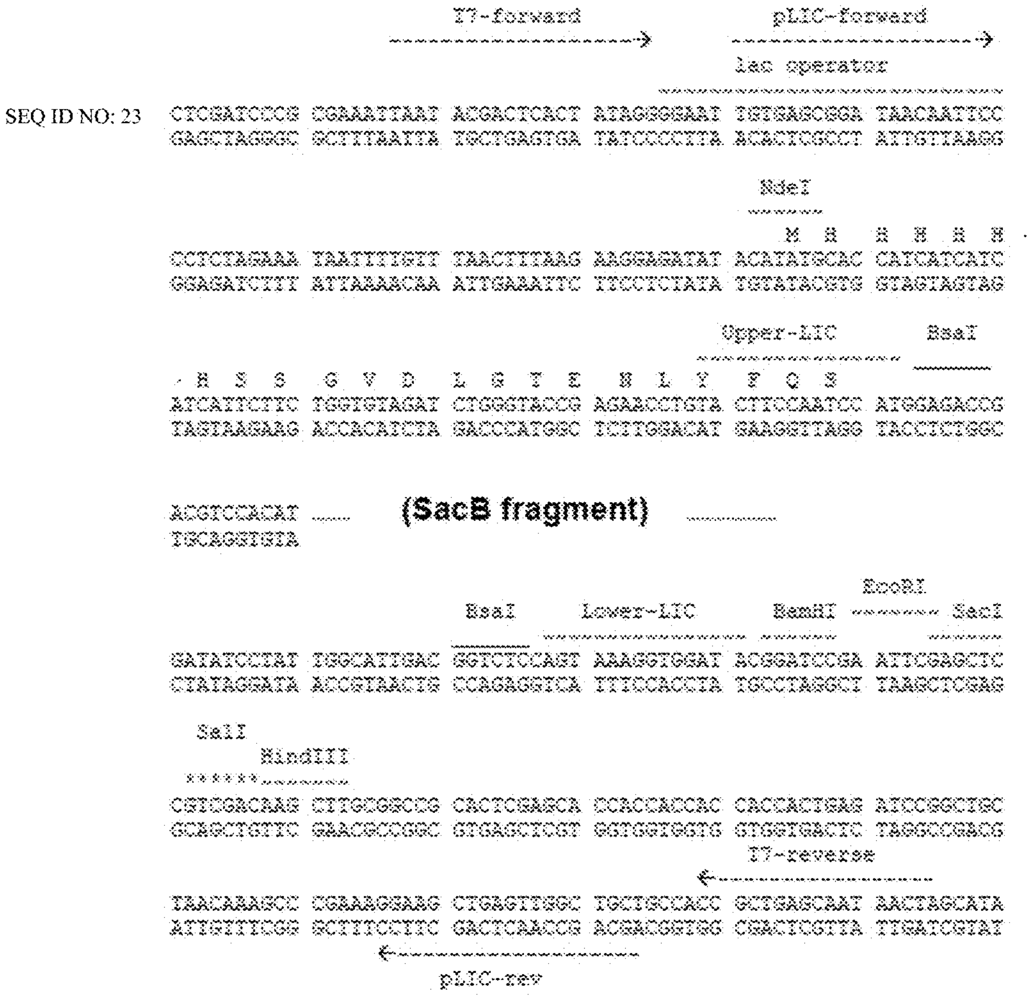
FIG. 1 shows cloning sites of pNIC28a-Bsa4 expression vector. Shown are a first half (SEQ ID NO: 24), which is connected to the 5' end of the SacB fragment, and a second half (SEQ ID NO: 25), which is connected to the 3' end of the SacB fragment, of the pNIC28a-Bsa4 expression vector (SEQ ID NO: 23). The amino acid sequence of the N-terminal protein His-tag having Tobacco Etch Virus (TEV) Protease Substrate Sequence (SEQ ID NO: 26) encoded in the vector is also shown.

After extensive and in-depth research as well as continuous and repeated exploration, the present inventors have developed a protein vaccine capable of stimulating $CD8^+$ T cell immunity for the first time, and the protein vaccine possesses advantages, such as low production cost and convenient control. Additionally, compared with existing vaccines, the vaccine of the present invention can also simultaneously stimulate $CD4^+$ T cell immunity. Experiments demonstrate that the protein vaccine of the present invention is effective in stimulating $CD8^+$ cells via MHC-I antigen presenting pathway. The present invention has been completed based on the above findings.

In particular, the present inventors have unexpectedly found that a multi-antigen fusion protein vaccine connected through cleavage site of cathepsin can be effectively presented by antigen-presenting cells via MHC-I pathway. In vitro and in vivo experiments have shown that the protein vaccine can effectively stimulate $CD8^+$ T cells, and also have the ability to stimulate $CD4^+$ T cells.

Terms

As used herein, the terms "protein of the present inventive", "fusion protein of the present invention", "artificial multi-antigen fusion protein", "antigen fusion protein", "fusion protein of the present invention stimulating $CD4^+$ and $CD8^+$ T cell immune responses" can be interchangeably used, and refer to an artificial recombinant protein having a structure of Formula I and capable of effectively and simultaneously activating $CD4^+$ and $CD8^+$ T cell immune responses.

Lysosome and MHC-I Pathway

Polypeptide antigens of short fragment (such as commercially-available T.SPOT.TB kit used to stimulate antigens of human antigen presenting cells) can not only enter lysosome and can be presented to MHC-II molecules, but also can be absorbed into cytoplasm by presenting cells, processed and presented to MHC-I class molecules. Protein antigens are firstly endocytosed by antigen-presenting cells, and then pass through early phagosome, late phagosome, and finally enter into lysosome. In general, proteins that enter lysosomes are completely degraded to amino acids. However, under certain situation, a protein will gradually degrade, and the resulting polypeptide can bind to MHC-II molecules located at lysosomal to form a relatively stable complex, presented to the cell surface, and stimulate $CD4^+$ T cell immunity. In general, protein antigens do not leak from lysosomes into cytoplasm and therefore do not enter MHC-I pathway to stimulate $CD8^+$ cells. The present inventors have unexpectedly found that the antigen fusion protein specially designed in the present invention can not only stimulate $CD8^+$ T cells, but also retain the original function of stimulating $CD4^+$ T cell.

The major protease in lysosomes of antigen-presenting cells is cathepsin S. Leu-Arg-Met-Lys (SEQ ID NO: 9) is a preference sequence for cathepsin S. In the present invention, Leu-Arg-Met-Lys (SEQ ID NO: 9) is preferably used to connect a group of antigen segments to form a new artificial multi-antigen fusion protein and stimulate $CD4_+$ and $CD8^+$ T cells.

Common antigen polypeptides of short fragment (generally ≤70aa, ≤60aa or shorter) can be directly absorbed into cytoplasm by antigen-presenting cells, and thus presented to MHC-class 1 molecules. Common protein antigens can only be endocytosed into lysosomes by antigen-presenting cells, and the common mature protein in lysosome only binds to MHC-II, and only stimulates $CD4^+$ T cells.

In contrast, the artificial multi-antigen fusion protein of the present invention is endocytosed into lysosomes by antigen presenting cells, and then cleavage occurs firstly in the ligation sequence in the presence of cleavage sites of cathepsin, such as cathepsin S, thereby rapidly generating a group (plurality) of polypeptides as well as achieving and facilitating cross-presentation, and simultaneously stimulating $CD8^+$ T cells and $CD4^+$ T cells.

Experiments of the present invention show that after the fusion protein of the present invention enters lysosomes, the fusion protein still disappears rapidly even lysosomal function is inhibited, indicating that the protein of the present invention or cleavage produces thereof in lysosomes can leak into cytoplasm.

Fusion Protein that Stimulates $CD4^+$ and $CD8^+$ T Cell Immune Response

In the present invention, a single protein, i.e., a multi-antigen fusion protein, is provided, which is formed by connecting a plurality of antigen epitopes (or antigen segments) and used for specific cellular immunoassays and as a prophylactic and therapeutic vaccine.

In the multi-antigen fusion protein of the present invention, there are at least one, more preferably 2, 3, 4, 5 or more (e.g., any positive integer of 6-20) $CD8^+$ T cell epitopes.

In the multi-antigen fusion protein of the present invention, at least one, more preferably two, three, four, five or more (e.g., any positive integer of 6-20) $CD4^+$ T cell epitopes are included.

In the present invention, the sequence of antigen segment may be from any polypeptide capable of stimulating immune response, preferably a sequence capable of stimulating $CD4^+$ or $CD8^+$ T cell responses (i.e., T cell epitopes).

Cathepsin is a group of cysteine proteases, the main role of which is to degrade lysosomal proteins. The known primary function of cathepsin-S is to participate in antigen presentation of MHC-2.

In the multi-antigen fusion protein of the present invention, these polypeptides containing $CD8^+$ T cell epitope and $CD4^+$ T cell epitope may be joined by recognition sites of cathepsin in any antigen presenting cell, and preferred Leu-Arg-Met-Lys (SEQ ID NO: 9) sequence for cathepsin S is preferably used.

In another preferred embodiment, several other cleavage sites of cathepsin B and K, which are relatively more expressed in presenting cells, may be used; for example, Met-Lys-Arg↓-Leu (SEQ ID NO: 10) is the cleavage site of cathepsin B, and His-Pro-Gly↓-Gly (SEQ ID NO: 11) is the cleavage site of cathepsin K. However, the effect of cleavage site of cathepsin S is particularly excellent.

In another preferred embodiment, different cleavage sites of cathepsin S can be used in the artificial multi-antigen fusion protein, including, but not limited to, Arg-Cys-Gly↓-Leu (SEQ ID NO: 12), Thr-Val-Gly↓-Leu (SEQ ID NO: 13), Thr-Val-Gln↓-Leu (SEQ ID NO: 14), X-Asn-Leu-Arg↓ (SEQ ID NO: 15), X-Pro-Leu-Arg↓ (SEQ ID NO: 16), X-Ile-Val-Gln↓ (SEQ ID NO: 17) and X-Arg-Met-Lys↓ (SEQ ID NO: 18); wherein X-Arg-Met-Lys↓ (SEQ ID NO: 18) and X-Asn-Leu-Arg J (SEQ ID NO: 15) are preferred linking cleavage sites, where X is any amino acid and ↓ is the cleavage site.

Any protein may be used into the present invention. In general, the sequence covered by the multi-antigen fusion protein accounts for more than 40% of the protein, and in a preferred embodiment, at least 50%, 60%, 70%, 80%, 90%, preferably 100% of the sequence of protein antigen is covered by the antigen fusion protein.

As a preferred example of the present invention, the coverage of HPV16-E7 multi-antigen fusion protein is 100%. Of course, even if the coverage is reduced, it is sometimes feasible, especially when the MHC-I antigen epitope in a target protein is less and distinct. For example, in a preferred embodiment of the present invention, the coverage of OVA is 40% because OVA has only a single MHC-I antigen epitope and the selected fragment includes the epitope.

The multi-antigen fusion protein may cover more than one antigenic protein. In another preferred embodiment, the antigen fusion protein of *tubercule bacillus* of the present invention covers both ESAT6 and CFP10 protein sequences, which may reduce the cost of production and facilitate quality control.

The artificial multi-antigen fusion protein of the present invention is different from natural proteins (such as proteins or tumor antigens from viruses, bacteria, parasites). One of the main differences is the loss of spatial structure of the natural protein and therefore does not possess the function of a natural protein, thus avoiding the potential hazards of, for example, pathogen proteins (such as viral capsid proteins).

The artificial multi-antigen fusion protein of the present invention is also different from the antigen polypeptide of short fragment (e.g., antigen peptide and epitope polypeptide of ≤70 or ≤60 amino acids). One of the main differences is that the protein of the invention has a large molecular weight and belongs to a macromolecule protein (rather than a small molecule polypeptide), and thus the pathway into a cell is not the same, resulting in that the pathway through which the antigen is presented, and the mode and mechanism for stimulating T cells are different from those of the antigen polypeptides of short fragment.

Preparation Method and Engineered Cell

Once the antigen protein sequence is determined, the protein of the present invention can be obtained by mass production using recombinant method. Generally, encoding DNAs artificially synthesized are cloned into an expression vector, transferred into a cell and then isolated from a host cell or a fermentation product by conventional methods.

A typical method for preparing an antigen fusion protein comprises steps of:

Constructing an artificial multi-antigen fusion protein according to the amino acid sequence of the protein antigen, and the multi-antigen fusion protein comprises or consists of a series of antigen segments of a specific length, wherein each antigen segment is connected by the same or different cleavage sites of cathepsin (e.g., leu-Arg-Met-Lys, SEQ ID NO: 9).

In addition, the cells used to express the fusion protein of the present invention are also included in the present invention. "Host cells" include prokaryotic cells and eukaryotic cells. Commonly used prokaryotic cells are *E. coli*. Commonly used eukaryotic cells include, but are not limited to, yeast cells, insect cells, and mammalian cells. As a preferred embodiment of the present invention, the used host cells are *Escherichia coli*, such as BL21 (DE3) and yeast, and CHO cells.

Vaccine Composition and Pharmaceutical Composition

In the present invention, the use of the fusion proteins of the invention is provided, for example, for immuno-diagnosis and preparation of vaccines.

Immunological diagnosis includes skin test and T cell dot enzyme immunoassay. The skin test is to immunize a subject with the multi-antigen fusion protein of the present invention, and then the skin reaction of the individual is observed to determine whether the individual has been exposed or infected with similar antigens. As a preferred embodiment of the present invention, the immuno-diagnosis is to use the fusion protein of the present invention as a source of stimulation to detect T cell immune response of an individual. For example, generation of gamma interferon after stimulating T cells of an individual with ESAT6-CFP10 multi-antigen fusion protein of the present invention can be observed to determine whether a patient is infected with tuberculosis or infection stage or prognosis.

Vaccines include prophylactic vaccines and therapeutic vaccines. The latter is mainly related to the activation of T cells, especially $CD8^+$ killer T cells (CTL). The activation of CTL cells is limited by MHC-I molecules. As a preferred embodiment of the present invention, it has been demonstrated in vitro that HPV16-E7 multi-antigen fusion protein of the present invention can be endocytosed by human antigen presenting cells and activate antigen presenting cells. In another preferred embodiment, the OVA multi-antigen fusion protein of the present invention is used as a model to demonstrate that it can be processed by antigen presenting cells and presented to MHC class I molecules.

Uses

In the fusion protein of the present invention, recognition sequences of cathepsin in the endosome and lysosome of antigen presenting cells are used to connect a plurality of antigen epitope peptides containing $CD4^+$ and $CD8^+$ epitopes into a single protein, which, after expression and purification, can be directly used in immune diagnosis or as a prophylactic and therapeutic vaccine.

When used as a prophylactic and therapeutic vaccine, the protein or composition of the present invention can be injected into an animal directly or with an adjuvant or used in vitro with a cell therapy. For example, it is added into DC/NK cell culture to stimulate the production of specific antigen presenting cells and then to stimulate the production of specific $CD8^+$ T cells (CTL) in vivo/in vitro with the antigen presenting cells.

In the present invention, these externally sensitized specific antigen presenting cells and/or in vitro produced CTL antigens can be returned to the body of a corresponding subject for antiviral, antitumor and other different uses.

In the present invention, the protein or in vitro sensitized cells (or corresponding formulation) of the invention are preferably administered to a subject by the following administration mode: intravenous injection, perfusion, subcutaneous injection, transdermal administration, and the like.

Main advantages of the present invention include:

(1) It has been found for the first time that the artificial multi-antigen fusion protein of the present invention can be efficiently presented onto MHC-I molecules.

(2) It has been found for the first time that a single multi-antigen fusion protein instead of several antigen short peptides, can specifically stimulate human T cells to release gamma interferon.

(3) It has been demonstrated for the first time that the antigen fusion protein of the present invention can be phagocytosed by antigen-presenting cells and activate $CD8^+$ cells.

(4) The fusion protein of the present invention can be used in the development of reagents and techniques for immunodiagnosis. For example, specific cellular immunity is detected by skin tests, or specific cellular immunity is detected by ELISPOT assays.

(5) The fusion protein of the present invention can be used in the development of therapeutic or prophylactic drugs or vaccines, including DC cells sensitized by the fusion protein of the present invention and/or CTL cell preparation, and the industrial application value is immeasurable.

(6) Compared with a conventional solution using a group of short fragment polypeptides, the cost of the method and product of the present invention is significantly reduced (typically at least 80% or more); and quality control is easy and huge amount of manpower, material and time can be saved.

The invention will be further illustrated with reference to the following specific examples. It is to be understood that these examples are only intended to illustrate the invention, but not to limit the scope of the invention. For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer. Unless otherwise stated, the percentages and parts are percentages by weight and parts by weight.

Example 1

Clone of Multi-Antigen Fusion Protein

The antigen fusion protein was designed according to the amino acid sequence of the protein. The antigen fusion protein was formed by connecting a series of polypeptide fragments (short fragment antigen peptide) of 25-35 amino acids in length, and the antigen peptides are ligated by the same preferred sequence of cathepsin S (Leu-Arg-Met-Lys, SEQ ID NO: 9).

Codons in the DNA encoding the antigen fusion protein are optimized into *E. coli* preferred codons. DNA coding sequences were prepared by whole artificial synthesis and TACTCCCATATATAT (SEQ ID NO.: 7) was added at 5'-end and TATCCACCTTTACTGTTA (SEQ ID NO.: 8) was added at 3'-end. Synthesized DNA molecules were treated with T4 DNA polymerase and dCTP for 30 minutes.

A conventional pNIC28-Bsa4 vector (obtained from Oxford University; U.S. Pat. No. 8,148,100 B2; GenBank ID: EF198106) was digested with BsaI for 1 hour. The important components involved in the expression of the clone in this vector are shown in FIG. 1. The linearized vector was isolated by 1% agarose gel electrophoresis and treated with T4 DNA polymerase and dGTP for 30 minutes. After two products from T4 DNA polymerase treatment were mixed, regular competent *E. coli* DN5α was transformed, and inoculated into a plate, and mono colony was picked up for culture. Positive colonies were identified by PCR performed on the culture.

Figure 2:
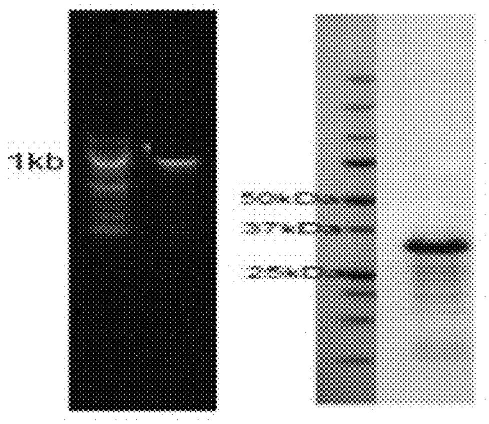
FIG. 2 shows electrophoresis identification of PCR products of *Escherichia coli* containing ESAT6/CFP10 gene (left) and SDS-PAGE electrophoresis analysis of purified ESAT6/CFP10 multi-antigen fusion protein (right).
Figure 3:
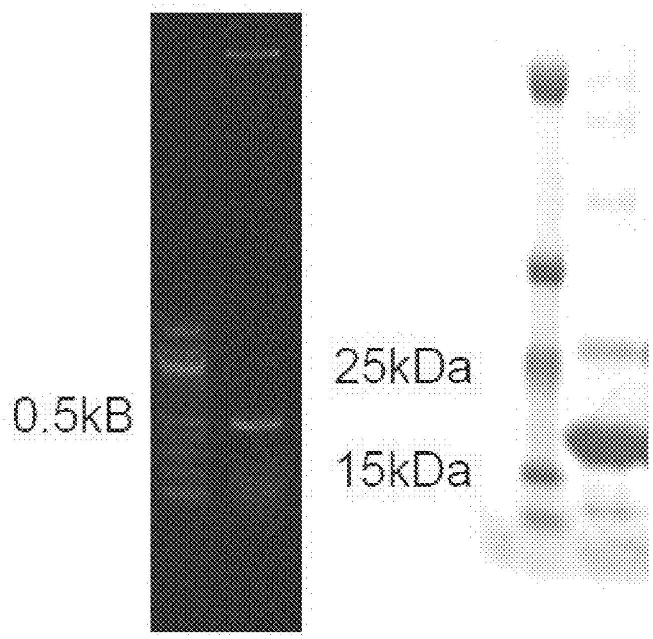
FIG. 3 shows electrophoresis identification of PCR products of *Escherichia coli* containing OVA: 242-352 gene (left) and SDS-PAGE electrophoresis analysis of purified OVA: 242-352 multi-antigen fusion protein (right).
Figure 4:
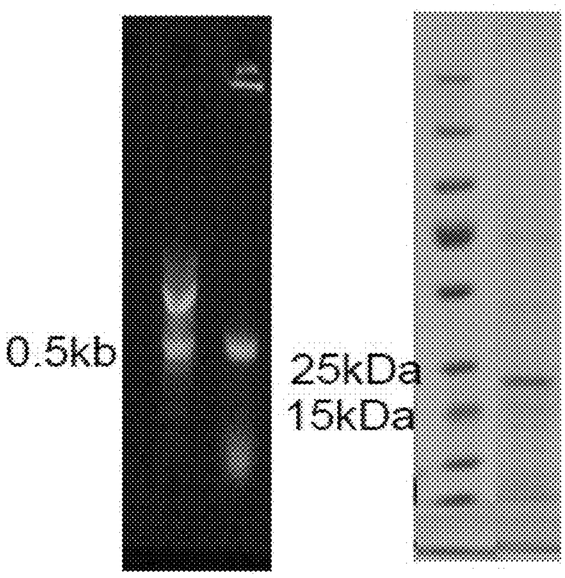
FIG. 4 shows electrophoresis identification of PCR products of *Escherichia coli* containing HPV16-E7 gene (left) and SDS-PAGE electrophoresis analysis of purified HPV16-E7 multi-antigen fusion protein (right).

Results are shown in FIGS. 2, 3 and 4, indicating that the size of the coding sequence of the obtained fusion protein and molecular weight of the protein are consistent with the design or predicted value.

The amino acid and nucleotide sequences of each multi-antigen fusion protein are shown as below.

| Name of Protein | Amino acid sequence | Nucleotide sequence |
|---|---|---|
| ESAT6-CFP10 antigen fusion protein (also named as "TB-antigen fusion protein") | SEQ ID NO.: 1 | SEQ ID NO.: 2 |
| OVA antigen fusion protein | SEQ ID NO.: 3 | SEQ ID NO.: 4 |
| HPV16-E7 antigen fusion protein | SEQ ID NO.: 5 | SEQ ID NO.: 6 |

```
SEQ ID NO.: 1
MAEMKTDAAT LAQEAGNFER ISGDLKTQID QVESTLRMKT QIDQVESTAG SLQGQWRGAA    60
GTAAQAAVVR FQELRMKAQA AVVRFQEAAN KQKQELDEIS TNIRQAGVQY SRLRMKIRQA   120
GVQYSRADEE QQQALSSQMG FLRMKMTEQQ WNFAGIEAAA SAIQGNVTSI HSLLDEGKQS   180
LRMKHSLLDE GKQSLTKLAA AWGGSGSEAY QGVQQKWDAL RMKYQGVQQK WDATATELNN   240
ALQNLARTIS EAGQAMASLR MKISEAGQAM ASTEGNVTGM FA                      282

SEQ ID NO.: 2
caaatcgatc aagtggaaag taccgcaggt agcctgcagg gtcagtggcg tggtgcagca   180
ggcaccgcag cacaggcagc agttgttcgt tttcaagaac tgcgcatgaa agcccaggca   240
gccgtggtgc gcttccaaga agccgcaaat aaacagaaac aagagctgga tgaaatcagc   300
accaatattc gtcaggcagg cgttcagtat agccgtttac ggatgaaaat tcgtcaagcc   360
ggtgtgcagt attcacgtgc agatgaagaa cagcagcaag cactgagcag ccagatgggt   420
```

-continued

| Name of Protein | Amino acid sequence | Nucleotide sequence |
|---|---|---|

```
tttttaagaa tgaaaatgac cgagcagcag tggaattttg caggtattga agcagccgca   480
agcgcaattc agggtaatgt taccagcatt catagcctgc tggacgaagg taaacagagc   540
ctgcggatga agcatagtct gttagatgaa ggcaaacagt cactgaccaa actggcagca   600
gcatggggtg gtagcggtag cgaagcatat cagggtgttc agcagaaatg ggatgcatta   660
cgtatgaagt atcagggcgt gcaacaaaag tgggacgcaa ccgcaaccga actgaataat   720
gcactgcaga atctggcacg taccattagt gaagccggtc aggcaatggc cagcttacgc   780
atgaagattt ctgaagcagg ccaagctatg gcaagcaccg aaggcaatgt gaccggtatg   840
tttgcataa                                                           849

SEQ ID NO.: 3
MLVLLPDEVS GLEQLESIIN FEKLTEWTSS LRMKLESIIN FEKLTEWTSS NVMEERKIKV    60
YLPRMKMEEK YNLTSVLMAM GITDVFSSSA NLSGISSAES LKISQAVHAA HAEINEAGRL   120
RMKISQAVHA AHAEINEAGR EVVGSAEAGV DA                                 152

SEQ ID NO.: 4
atgctggttc tgctgccgga tgaagttagc ggtctggaac agctggaaag cattatcaat    60
tttgaaaaac tgaccgaatg gaccagcagc ctgcgtatga aactggaatc catcattaac   120
ttcgagaaac tgacagagtg gacaagcagc aatgttatgg aagaacgtaa aatcaaagtg   180
tacctgcctc gcatgaaaat ggaagagaaa tataacctga ccagcgttct gatggcaatg   240
ggtattaccg atgtttttag cagcagcgca aatctgagcg gtattagcag cgcagaaagc   300
ctgaaaatta gccaggcagt tcatgcagca catgccgaaa ttaatgaagc aggtcgtctg   360
cggatgaaaa tttcacaggc cgtgcatgct gcccatgcag aaatcaacga agctggccgt   420
gaagttgttg gtagtgccga agccggtgtt gatgcataa                          459

SEQ ID NO.: 5
MHGDTPTLHE YMLDLQPETT DLYCYEQLND SSEEELRMKE QLNDSSEEED EIDGPAGQAE    60
PDRAHYNIVT FCCKLRMKHY NIVTFCCKCD STLRLCVQST HVDIRTLEDL LMGLRMKIRT   120
LEDLLMGTLG IVCPICSQKP                                               140

SEQ ID NO.: 6
atgcatggtg ataccccgac cctgcatgaa tatatgctgg atctgcaacc ggaaaccacc    60
gatctgtatt gttatgagca gctgaatgat agcagcgaag aggaattacg catgaaggaa   120
cagctgaacg attcaagcga agaagaggac gaaattgacg gtccggcagg tcaggcagaa   180
ccggatcgtg cacattacaa cattgttacc ttttgttgca aactgagaat gaaacactac   240
aatatcgtga ccttctgctg taaatgtgat agcaccctgc gtctgtgtgt tcagagcacc   300
catgttgata ttcgtacatt agaggacctg ctgatgggcc tgcggatgaa aattcgtacc   360
ctggaagacc tgttaatggg caccctgggt attgtttgtc cgatttgtag ccagaaaccg   420
taa                                                                 423
```

In addition, LC-MS analysis also showed that the measures molecular weight of purified TB-antigen fusion protein (30974 Da), OVA antigen fusion protein (16589 Da) and HPV16-E7 antigen fusion protein (16231 Da) were consistent with the predicted values.

Example 2

Expression of Antigen Fusion Protein Plasmid DNA of positive colonies containing encoding sequence of the artificial multi-antigen fusion protein was extracted and transformed into *Escherichia coli* BL21 (DE3).

Transformed single colonies were inoculated into low salt LB broth and incubated overnight at 37° C. The culture was diluted at 1:100 in low salt LB broth, incubated at 37° C. with shaking until OD600=1.0 and cooled to 18° C. 0.2 mM IPTG was added for inducing expression of protein. Cells were incubated at 18° C. for another 16 hours and then centrifuged at 4000 rpm. The cells were collected and re-suspended in phosphate buffer.

Example 3

Purification of Antigen Fusion Protein (a) Purification of ESAT6-CFP10 and OVA Antigen Fusion Protein Cells were lysed by ultrasonic method and inclusion bodies were collected by centrifugation. The inclusion bodies were dissolved in denaturation buffer (8 M urea in HEPES buffer at pH 7.4) and passed through a Ni-NTA column, and the antigen fusion protein containing histidine label bound to the column. After impurity proteins were removed by sufficient washing, the antigen fusion protein was eluted with urea elution buffer. The eluted antigen fusion protein was firstly diluted 8-fold with PBS containing 0.5 M arginine (pH 9.5) and the urea was removed through dialysis against PBS (right panel in FIG. 2 and right panel in FIG. 3).

(b) Purification of HPV16-E7 Antigen Fusion Protein

The cells were lysed by ultrasonic method. The supernatant containing target proteins was collected by centrifugation and passed through a Ni-NTA column. The histidine-labeled antigen fusion protein was bound to the column. After impurity proteins were removed by sufficient washing, HPV16-E7 antigen fusion protein was eluted with an elution buffer containing imidazole (right panel in FIG. 4).

Example 4

Intake of Antigen Fusion Protein by Antigen Presenting Cells

Human peripheral blood lymphocytes PBMCs were isolated from blood of voluntary blood donors by Ficoll and washed. The cell concentration was adjusted to $2\times10^6$/ml in cell culture medium and 5 ml of cell suspension was placed in a cell culture flask. HPV16-E7 antigen fusion protein (50 μg/ml) was added or FITC-HPV16-E7 (5 μg/ml) was added at the same time, and cultured hours at 37° C. and 5% $CO_2$ for 24 hours and for another 12 hours. Cells were stained with anti-human CD54 antibody at 4° C. for 30 minutes and analyzed by flow cytometry. After treated for 13 hours, the cells were treated by EDTA, harvested and washed with 1 ml of ice-cold FACS buffer (2% FCS in PBS) for two times. And then a commercially available PE-tagged monoclonal antibody 25. D1-16 was added to a concentration of 0.6 μg/ml, and incubate at 4° C. for 30 min. Cells were washed for three times with FACS buffer and the cells were re-suspended in 0.2 ml of FACS fixation buffer (BD) and analyzed by flow cytometry.

Figure 5:
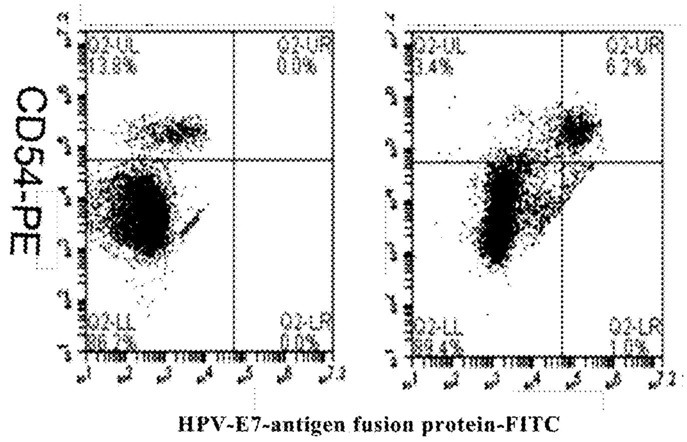
FIG. 5 shows the flow cytometry analysis of normal human PBMC which is treated by HPV16-E7 multi-antigen fusion protein, and the two-parameter scatter plot shows distribution of CD54 and antigen in PBMC. CD54 is labeled with PE and the antigen is labeled with FITC.

Results showed that the major cells which phagocytose multi-antigen fusion protein were CD54 positive cells (FIG. 5).

Example 5

Detection of γ-Interferon Secreting T Cells in Patients with Antigen Fusion Protein In this example, the ability of TB-antigen fusion protein to stimulate CD8+ T cells was tested by γ-interferon release assay. The method is described as below:

After peripheral blood mononuclear cells were isolated from tuberculosis sputum smear positive patients, the cell concentration was adjusted to $5\times10^6$ live cells/ml. 50 μl of the above mentioned cell suspension was added into negative wells, positive wells (with CONA as stimulating source), detection wells (With TB-antigen fusion protein as stimulating source), and control wells (with antigen T-spot A and T-spot B in the commercially available T-SPOT.TB kit from Oxford Immunology Technology Ltd., as stimulating source; or with mature CFP10-ESAT6 fusion natural protein (marked as TB-ESAT6-CFP10) as control stimulating source)) respectively.

Cells were incubated at 37° C., 5% $CO_2$ for 16-20 hours, plates were washed, and 50 μl of labeled antibody working solution was added, and incubated at 2-8° C. for 60 minutes. Afterwards, the plates were washed, and 50 μl of BCIP INBT substrate solution was added, incubated at room temperature in darkness, dried, and counted. Results were judged according to the instruction of T-SPOT.TB kit: when the number of spots in a blank control well is 0-5, the number of spots in an antigen-containing well—the number of spots in a blank control well ≥6; or when the number of spots in a blank control well is 6-10, the number of spots in an antigen-containing well ≥2 times of the number of spots in a blank control well.

Figure 6:
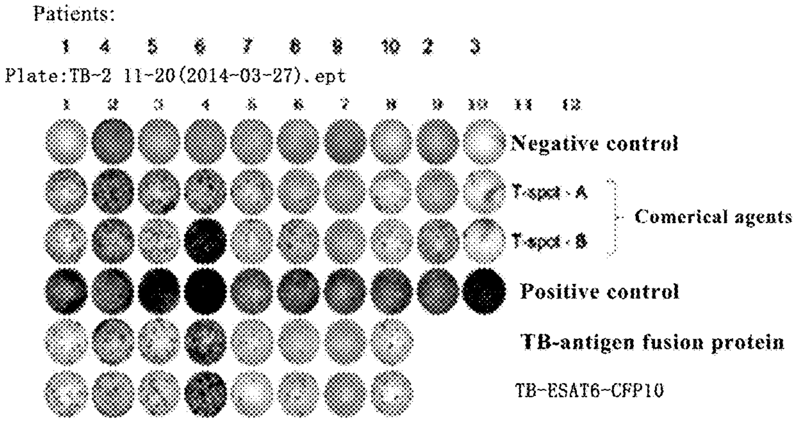
FIG. 6 shows the spots formed after stimulated by ESAT6/CFP10 multi-antigen fusion protein, ESAT6/CFP10 mature protein, and antigens in a commercially-available T-SPOT.TB kit, respectively. The results show that for stimulation of total T lymphocytes, effects of ESAT6/CFP10 multi-antigen fusion protein and antigens in the commercially-available T-SPOT.TB kit are equivalent (above panel), while for the stimulation of $CD8^+$ lymphocytes, effects of ESAT6/CFP10 multi-antigen fusion protein are significantly better than those of ESAT6/CFP10 mature protein (below panel).
Figure 6:
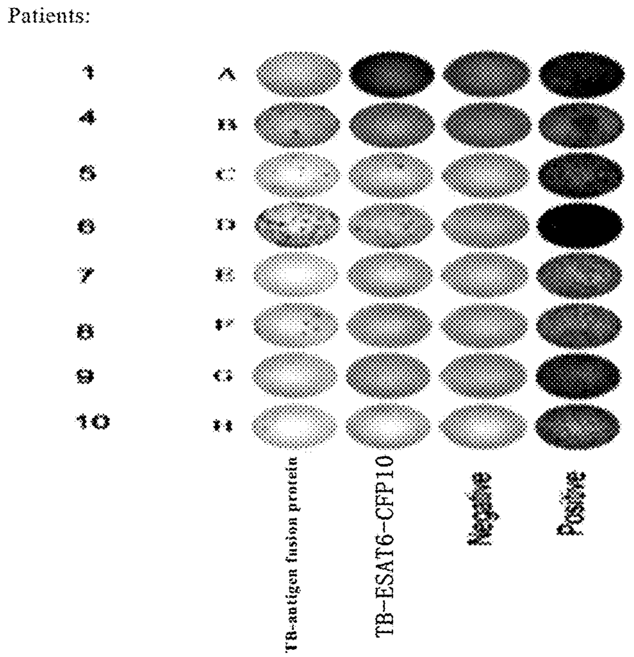

The results showed that effects obtained from stimulation with ESAT6/CFP10 antigen fusion protein was consistent with those obtained from stimulation with antigens in T-SPOT.TB kit (FIG. 6).

In addition, after $CD4^+$ T cells of the patient were removed by using specific anti-CD4 magnetic beads, remaining T cells were mainly $CD8^+$ T cells, and multi-antigen fusion protein and CFP10 mature protein were compared on this basis.

Results showed that TB-antigen fusion protein of the present invention exerted a significant stimulating effect on $CD8^+$ T cells. In contrast, the wild-type sequence of ESAT6-CFP10 mature protein exerted little effect on $CD8^+$ T cells (FIG. 6).

Example 6

In Vitro Induction of Specific $CD8^+$ T Cells by Antigen Fusion Protein-Loaded DCs Preparation of antigen-loaded DC cells: After mononuclear peripheral cells (PBMC) were isolated, part of the cells were frozen and the remaining cells were adjusted to a cell concentration of $1\times10^7$ cells/mL and incubated in conventional AIM-V culture for 2 hours. Suspended cells were removed (cryo-preserved) and AIM-V medium containing GM-CSF (1000 IU/ml) and IL-4 (50 IU/ml) was added and incubated at 37° C., 5% $CO_2$. HPV16-E7 antigen fusion protein (50 μg/ml) or recombinant HPV16-E7 protein (50 μg/ml) was added at day 3.

$CD8^+$ T cells were sensitized in vitro by antigen-loaded DCs: At day 5, adherent DC cells were collected, cryo-preserved PBMCs were thawed, in which CD8-positive cells were separated with CD8 beads, and CD8-negative cells were frozen. CD8 positive cells: DC cells were co-cultured in a 5:1 ratio and IL-2 100 IU/ml, IL-7 25 IU/ml were added. In addition, IL-2 (100 IU/ml) and IL-7 (25 IU/ml) were added every 2 days or half-volume of fluid was changed. On day 7, the frozen CD8-negative cells were thawed and treated with mitomycin. Afterwards, CD8-negative cells were added according to 1/10 of the number of CD8+ T cells for secondary stimulation. 50 μg/ml of corresponding protein was supplemented, and IL-2 100 IU/ml, IL-7 25 IU/ml were supplemented. IL-2 100 IU/ml and IL-7 25 IU/ml were supplemented every two days.

Preparation of antigen presenting cells: the suspended cells frozen at day 1 were thawed, and incubated in a plate coated with CD19 monoclonal antibody for 2 h. Non-adherent cells were discarded, CD19 positive cells were suspended in the culture medium. The cell concentration was adjusted to $5\times10^5$/ml, 2 ml of the cell suspension was cultured at 37° C., 5% $CO_2$ for 48 h, and IL-4 was added to a concentration of 100 μg/ml.

Effects of in vitro induction of specific $CD8^+$ T by multi-antigen fusion protein-loaded DCs evaluated through y-interferon release assay: $5\times10^4$ cells/50 μl of CD19 positive cells were added to a 96-well plate, and corresponding proteins (HPV16-E7 antigen fusion Protein (SEQ ID NO.: 5) or conventional recombinant HPV16-E7 protein) were added to 50 μg/ml, and incubated at 37° C., 5% $CO_2$ for 2 h. After centrifugation, supernatant was discarded, and cells were re-suspended in 50 μl of fresh medium. $5\times10^4$ cells/50 μl of CD8 positive cells were added and incubated at 37° C. for 18 hr. The concentration of IFN-γ in the supernatant was measured by ELISA.

Results are shown in Table 1: $CD8^+$ T cells can be sensitized in vitro and re-activated by antigen fusion protein HPV16-E7-loaded DC, effects of the antigen fusion protein is much higher than that of the control protein HPV-E7, i.e., compared with the recombinant HPV16-E7 protein as the control, the release of gamma-interferon caused by the fusion protein of the present invention was increased by 372.5%. (152.7−58.2)/(2.5−(−17.5))−1)*100%=372.5%).

TABLE 1

Effects of HPV16-E7 antigen fusion protein and recombinant HPV16-E7 protein on in vitro stimulating DC to induce specific $CD8^+$ T cells detected through γ-interferon release assay

| Concentration of IFN-γ (ng/l) | | | |
|---|---|---|---|
| | $CD8^+$ CD19 + antigen | $CD8^+$ CD19 (negative control) | Net release of IFN-γ |
| HPV16-E7-antigen fusion protein | 152.7 | 58.2 | 94.5 |
| HPV16-E7-natural protein | 2.5 | −17.5 | 20.0 |
| Non-antigen | −29.0 | −27.3 | −1.7 |

Example 7

Skin Sensitive Test for Tuberculosis

A guinea pig weighing about 250 g was intradermally injected with 0.1 ml of PPD and the skin reaction was observed at 24 hours. Skin reaction-negative guinea pigs were randomly divided into 5 groups, subcutaneously injected with 0.2 ml of 40 mg/ml of *Mycobacterium tuberculosis H*37Rv suspension at the inguinal, and immunized once every week for five times. One week after the fifth immunization, the guinea pigs were randomly divided into five groups. Furs on the back of guinea pig were plucked, 0.1 ml of positive control (PPD), negative control (tuberculosis-irrelevant recombinant protein), recombinant ESAT6-CFP10 protein, a mixture liquid of recombinant ESAT6-CFP10-antigen fusion protein (1 mg/ml, 0.1 mg/ml) were intradermally injected by alternative skin test respectively. The vertical diameter and horizontal diameter (mm) of skin redness at each injection spot on the back of a guinea pig were measured 24 hours after the injection, and average value was recorded.

Figure 7:
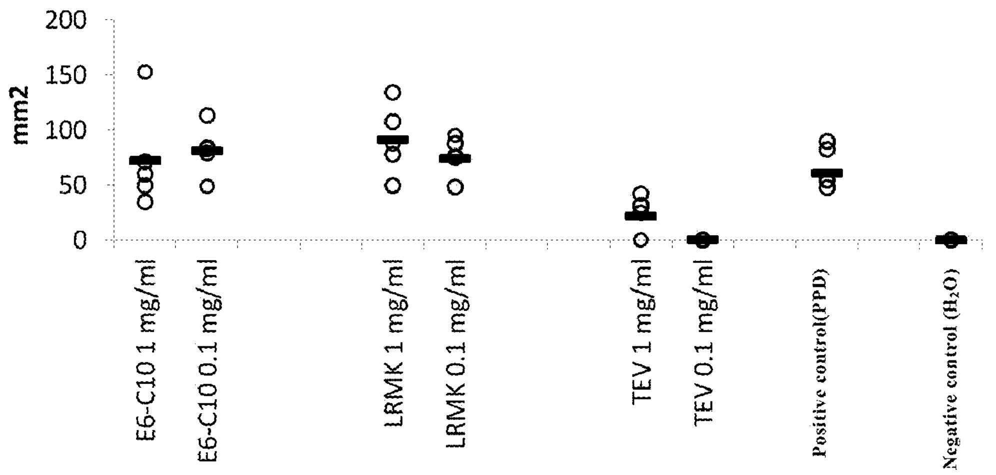
FIG. 7 shows results of skin test for ESAT6/CFP10 multi-antigen fusion protein. In the figure, results of skin test for four groups of guinea pigs sensitized by proteins/polypeptides derived from inactivated *Mycobacterium tuberculosis* H37Rv are shown. 0.1 ml of positive control (PPD), negative control, recombinant ESAT6/CFP10 multi-antigen fusion protein (marked as "LRMK" (SEQ ID NO: 9)), recombinant ESAT6-CFP10 mature protein (marked as "E6-C10") were intradermally injected by alternative skin test, and the area of red and swollen skin at each injection site of guinea pigs was measured 24 hours after injection.

Results of 24-hour skin reaction are shown in FIG. 7. In TB-antigen fusion protein group (SEQ ID NO: 1), the average diameter of skin induration is greater than that of PPD group and ESAT6-CFP10 natural protein group. In the control group, no swelling, or induration reaction was observed on local skin of a guinea pig. This suggests that TB-antigen fusion proteins can be used in a skin test to effectively detect tuberculosis infections.

In the figure, E6-C10 represents ESAT6-CFP10-natural protein; LRMK (SEQ ID NO: 9) represents TB-antigen fusion protein, in which cleavage site of cathepsin S is used to connect each antigen segment, and sequence of which is shown in SEQ ID NO: 1; and TEV represents a control protein formed by replacing all cleavage sites of cathepsin S in SEQ ID NO: 1 with TEV cleavage site (cleavage site of non-cathepsin).

Example 8

Treatment and Delivery Mechanism of Antigen Presenting Cells on Antigen Fusion Proteins and Common Antigens In order to determine after antigen presenting cells intake antigen fusion proteins and are activated by antigen fusion proteins, whether T cell epitopes can be efficiently presented to MHC-I molecule ($CD8^+$ T cells can be only activated by presenting on MHC-I molecule, thereby producing cytotoxic reaction, and killing bacteria/virus-infected cells or cancerous cells). In the present example, OVA antigen fusion protein was designed, expressed and purified according to positions 242-352 of amino acid sequence of chicken ovalbumin (OVA), which contains MHC-1 epitope SIINFKL (SEQ ID NO: 20). And the OVA protein fragment OVA 255-340 containing the epitope was used as a control. The mouse dendritic cell line (DC2.4) was used as antigen presenting cells to study the presentation of SIINFEKL (SEQ ID NO: 21) in OVA antigen fusion protein. Finally, T cell receptor-like antibodies (identifying SIINFEKL (SEQ ID NO: 21)/MHC-I complex) were detected.

100 μg/ml of OVA protein fragment (or 30 μg/ml of OVA antigen fusion protein (SEQ ID NO: 3)) was mixed with DC2.4 cells, cultured in RPMI 1640(Sigma) containing 10% heat-inactivated fetal bovine serum (sigma), 2 mM L-glutamine (Sigma) for 13 hours, then stained with a commercially available 25.D1-16 antibody labeled with PE (the monoclonal antibody 25. D1-16 specifically recognizes MHC-1 molecule binding to SIINFEKL (SEQ ID NO: 21)), and washed by 1 ml of ice-cold FACS buffer (2% FCS in PBS) for two times. Afterwards, PE-labeled monoclonal antibody 25.D1-16 was added to a concentration of 0.6 pg/ml, and incubate at 4° C. for 30 min. Cells were washed for three times with FACS buffer, re-suspended in 0.2 ml of FACS fixation buffer (BD) and analyzed by flow cytometry.

Figure 8:
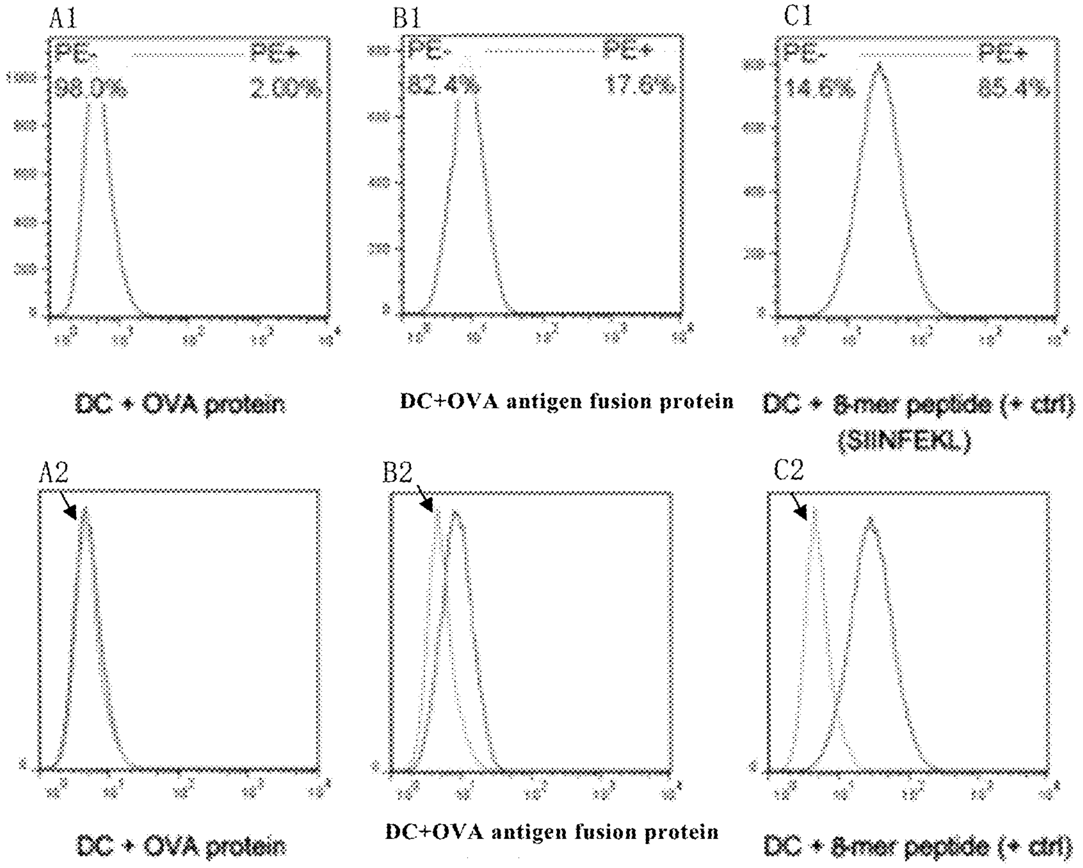
FIG. 8 shows flow cytometry analysis of distribution of SIINFEKL (SEQ ID NO: 21)—MHC-I on DC2.4 cells. Histograms show that SIINFEKL (SEQ NO: 21) peptide in OVA (242-252) multi-antigen fusion protein can be efficiently presented by DC cells at a concentration of 100 μg/ml (delivery efficiency is 17.6%). Whereas original protein fragments containing SIINFEKL (SEQ ID NO: 21) peptide can not be presented to MHC class I molecule.

Results are shown in FIG. 8. In the figure, the blue peak (indicated by the arrow) is DC+PBS.

As a positive control, 8 peptide (SIINFEKL, SEQ ID NO: 21) can directly bind to MHC-1 molecule on cell surface, so that more than 80% of the cells were positively stained (C1 and C2 in FIG. 8).

SIINFEKL peptide (SEQ ID NO: 21) in OVA natural protein can not be processed by DC cells and presented on MHC-1 molecule (A1 and A2 in FIG. 8). (Note: The blue and red peaks in FIG. 8A2 almost overlap).

Surprisingly, as a protein with large molecular weight, SIINFIKL peptide (SEQ ID NO: 22) in OVA-antigen fusion protein (SEQ ID NO: 3) can be efficiently processed by mouse dendritic cell line DC2.4 and presented to the cell surface, resulting in up to about 17.6% of cells being 25.D1-16 antibody positively-stained (B1 and B2 in FIG. 8).

Example 9

Anti-Tumor Effects of C57/BL6 Mice Immunized with Antigen Fusion Protein on Murine Melanoma Cell B16 Overexpressing Survivin or HPV-E7

2 mg/ml of antigen solution (control group: recombinant HPV-E7 protein, recombinant Survivin protein; experimental group: HPV-E7 antigen fusion protein (SEQ ID NO: 5), Survivin antigen fusion protein) was mixed with 1 mg/ml of MPL at equal volume to prepare an immunization suspension. Afterwards, 10 randomly assigned C57/B6 female mice aged 7-8 weeks and weighing 25 grams were subcutaneously injected at neck with 100 μl of immunization suspension on the 0 day, 21 day and 42 day.

Figure 9:
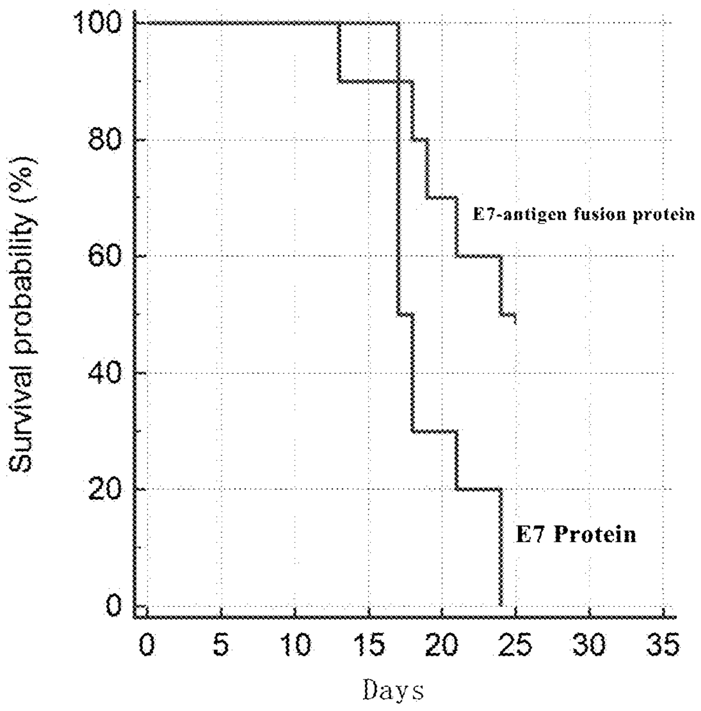
FIG. 9 shows survival-time curve for B16-HPV-E7 tumor-bearing mice (the date of inoculation of tumor cell is deemed as day 0).
Figure 10:
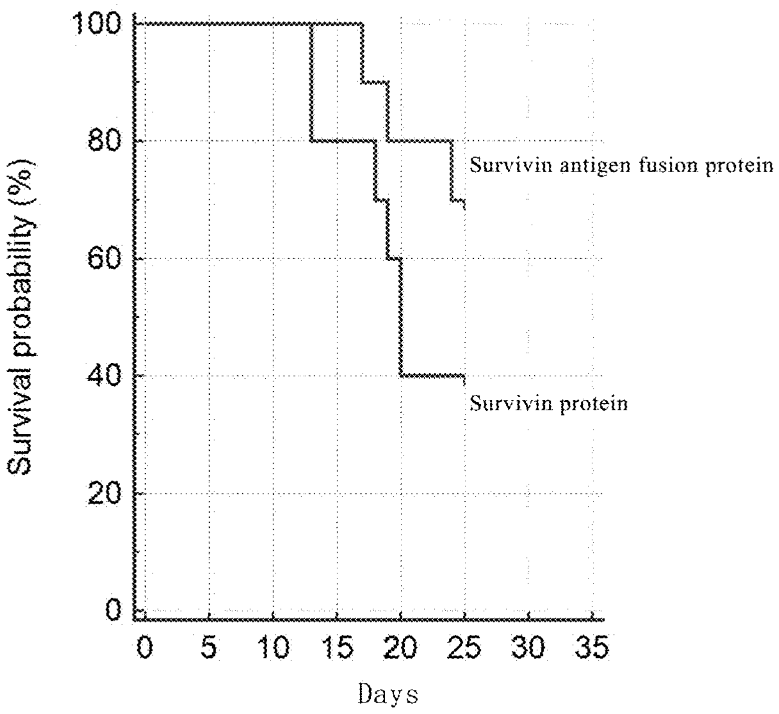
FIG. 10 shows survival-time curve for B16-survivin mice (the date of inoculation of tumor cell is deemed as day 0).

For each immunized mouse, 100 μl of homogeneously mixed mice B16 cells stably transfected with human HPV-E7 or Survivin were subcutaneously inoculated at right flank of the mice, and the amount of injected cells was $7\times10^5$ cells. The survival of mice was recorded and evaluated. Results are shown in FIG. 9 and FIG. 10.

The results showed that compared with the recombinant HPV-E7 protein control group, HPV-E7 antigen fusion protein of the present invention can significantly prolong the survival rate of mice (FIG. 9) and 50% of mice still survived on day 25; while all mice in recombinant protein control group were dead.

Compared with the recombinant Survivin protein, the Survivin antigen fusion protein of the present invention can significantly prolong the survival of mice (FIG. 10), and 70% of mice still survived on day 25; while only 40% of mice in the recombinant protein control group survived.

DISCUSSION

Prior to the present invention, clinically protein antigens were not successfully used as vaccines to stimulate $CD8^+$ cell immunity.

Production and quality control of protein-like vaccine are mature technology and many clinical drugs and vaccines (stimulating antibodies) are proteins. It would be ideal if vaccines that could stimulate $CD8^+$ T cell immunity can be produced by the proven method of producing protein. However, how to convert protein antigen presentation from endosome-lysosome-MHC-II pathway to cytoplasm-MHC-I pathway is a very challenging subject. Many immunologists and vaccine scientists are making efforts but there is no breakthrough yet.

Main obstacles include:

1. There are a lot of enzymes in Lysosomes, their function is generally to completely degrade a protein, and a protein will be degraded into amino acids instead of peptides. Therefore, a general recombinant protein antigen will be completely degraded and can not stimulate T cells.

2. Since lysosomal membrane is to isolate acid substances and cytoplasm in lysosome, lysosome is not an organelle which is easy to leak. Even a conventionally expressed protein or recombinant protein is not completely degraded, whether it can escape from or leak out of lysosome is unknown.

3. For protein antigens that can stimulate $CD4^+$ T cells, if a fusion protein, after $CD8^+$ antigen is added, is degraded and leaks into cytoplasm (stimulating $CD8^+$ T cells), whether the function of stimulating $CD4^+$ T cell will decrease or disappear, is also unknown.

In the present invention, the present inventors have designed a variety of antigen fusion proteins based on enzymatic principles and biological recombination techniques, and identified a novel structure of antigen fusion protein, after a huge amount of screening: a series of long peptides containing antigen segment are ligated by cleavage sites of cathepsin. When the antigen fusion protein is phagocytosed in a cell and enters into lysosome, cathepsin in lysosome will degrade the antigen fusion protein into polypeptides containing different antigen epitopes.

The experiments of the present invention have surprisingly confirmed that after the fusion protein with particular structure of the present invention is degraded, degraded polypeptides are capable of leaking out of lysosomes and entering into cytoplasm and being processed to MHC class I molecule, thereby initiating MHC-I antigen presenting pathway and in turn stimulating $CD8^+$ cells; and the original function of stimulating $CD4^+$ T cell can be retained or improved.

All documents mentioned in the present invention are incorporated herein by reference, as if each document were individually recited for reference. It is to be understood that those skilled in the art will be able to make various changes or modifications to the present invention after reading the teachings of the present invention, which also fall within the scope of the claims appended hereto.

The invention claimed is:

1. A fusion protein consisting of the following structure

Y-(A-C)n, wherein A is a polypeptide fragment 15-35 amino acids in length consisting of a sequence corresponding to a subsequence of a target protein amino acid sequence that is a bacterial antigen, a viral antigen, an autoimmune disease antigen, or a tumor associated antigen, C is a cleavage site of cathepsin S represented by Leu-Arg-Met-Lys (SEQ ID NO: 9), n is a positive integer ≥3, Y is absent or is a sequence represented by "Y0-B," wherein Y0 is a signal peptide sequence and/or a tag sequence and B is absent or a cleavage site of cathepsin S represented by Leu-Arg-Met-Lys (SEQ ID NO:9), and the C in the C-terminal "A-C" is absent.

2. The fusion protein of claim 1, wherein collectively the polypeptide fragments of the fusion protein cover ≥80% of the amino acid sequence of the target protein.

3. The fusion protein of claim 1, wherein collectively the polypeptide fragments of the fusion protein cover ≥90% of the amino acid sequence of the target protein.

4. The fusion protein of claim 1, wherein collectively the polypeptide fragments of the fusion protein cover 100% of the amino acid sequence of the target protein.

5. The fusion protein of claim 1, wherein the fusion protein is produced by selecting a target protein that is a bacterial antigen, a viral antigen, an autoimmune disease antigen, or a tumor associated antigen, and producing a nucleotide sequence encoding the following structure Y-(A-C)n, wherein A is a polypeptide fragment 15-35 amino acids in length consisting of a sequence corresponding to a subsequence of the target protein amino acid sequence, C is a cleavage site of cathepsin S represented by Leu-Arg-Met-Lys (SEQ ID NO: 9), n is a positive integer ≥3, Y is absent or is a sequence represented by "Y0-B," wherein Y0 is a signal peptide sequence and/or a tag sequence and B is absent or a cleavage site of cathepsin S represented by Leu-Arg-Met-Lys (SEQ ID NO:9), and the C in the C-terminal "A-C" is absent, and expressing the fusion protein in a host cell.

6. The fusion protein of claim 5, wherein collectively the polypeptide fragments of the fusion protein cover ≥80% of the amino acid sequence of the target protein.

7. The fusion protein of claim 5, wherein collectively the polypeptide fragments of the fusion protein cover ≥90% of the amino acid sequence of the target protein.

8. The fusion protein of claim 5, wherein collectively the polypeptide fragments of the fusion protein cover 100% of the amino acid sequence of the target protein.

9. A method for eliciting a CD4 or a CD8 response against a target protein in a subject, comprising:

producing the fusion protein according to claim 1; and administering the fusion protein to a subject.

10. The method according to claim 9, wherein the target protein is associated with a disease.

* * * * *